(12) United States Patent
Wilson et al.

(10) Patent No.: US 6,835,178 B1
(45) Date of Patent: Dec. 28, 2004

(54) ULTRASONIC BONE TESTING WITH COPOLYMER TRANSDUCERS

(75) Inventors: Kevin Wilson, Cambridge, MA (US); Hong Wang, Audubon, PA (US); Jay Stein, Boston, MA (US); Mitchell Thompson, Exton, PA (US); Klaus Kubierschky, North Reading, MA (US); Kyung Park, Berwyn, PA (US); Dick Cabral, Tewksbury, MA (US); Glen MacGibbon, Berwyn, PA (US)

(73) Assignee: Hologic, Inc., Bedford, MA (US)

( * ) Notice: Subject to any disclaimer, the term of this patent is extended or adjusted under 35 U.S.C. 154(b) by 50 days.

(21) Appl. No.: 09/595,074

(22) Filed: Jun. 16, 2000

Related U.S. Application Data

(60) Provisional application No. 60/140,638, filed on Jun. 23, 1999.

(51) Int. Cl.[7] ................................................ A61B 8/12
(52) U.S. Cl. ...................................................... 600/449
(58) Field of Search ................................ 600/437, 438, 600/442, 449, 463, 439; 381/114; 310/334, 335, 327; 427/100; 438/3; 29/25.35

(56) References Cited

U.S. PATENT DOCUMENTS

| | | | | |
|---|---|---|---|---|
| 4,156,800 A | * | 5/1979 | Sear et al. .................... | 381/114 |
| 4,424,465 A | * | 1/1984 | Ohigashi et al. ............. | 310/335 |
| 4,564,019 A | * | 1/1986 | Miwa .......................... | 600/424 |
| 4,774,959 A | | 10/1988 | Palmer et al. ......... | 128/660.06 |
| 4,917,097 A | * | 4/1990 | Proudian et al. ............. | 600/463 |
| 5,254,504 A | * | 10/1993 | Van der Spiegel et al. . | 427/100 |
| 5,307,816 A | * | 5/1994 | Hashimoto et al. .......... | 600/439 |
| 5,452,722 A | | 9/1995 | Langton ................. | 128/660.06 |
| 5,511,296 A | * | 4/1996 | Dias et al. ................... | 29/25.35 |
| 5,755,228 A | | 5/1998 | Wilson et al. ......... | 128/660.06 |
| 5,772,596 A | | 6/1998 | Forfitt et al. ................. | 600/449 |
| 5,840,029 A | | 11/1998 | Mazess et al. ............... | 600/437 |
| 5,935,073 A | | 8/1999 | Wilson et al. ............... | 600/449 |
| 6,004,272 A | | 12/1999 | Barry et al. ................. | 600/449 |
| 6,012,779 A | | 1/2000 | Morris ........................ | 300/459 |
| 6,013,031 A | * | 1/2000 | Mendlein et al. ............ | 600/442 |
| 6,027,449 A | | 2/2000 | Mazess et al. ............... | 300/459 |
| 6,038,752 A | * | 3/2000 | Finsterwald et al. ........ | 29/25.35 |
| 6,307,302 B1 | * | 10/2001 | Toda ........................... | 310/327 |
| 6,420,190 B1 | * | 7/2002 | Shimoda et al. ................ | 438/3 |

OTHER PUBLICATIONS

G.W. Petley et al., Broadband Ultrasonic Attenuation: are Current Measurement Techniques Inherently Inaccurate? Brit. J. Radiol. 68:1212–14 (1995).
R.L. Goldberg et al., In Vivo Imaging Using a Copolymer Phased Array, Ultrasonic Imaging 14:234–48 (1992).

* cited by examiner

*Primary Examiner*—Ali Imam
(74) *Attorney, Agent, or Firm*—Cooper & Dunham LLP

(57) ABSTRACT

Ultrasonic bone testing apparatus including a pair of spaced piezoelectric copolymer transducers for transmitting and receiving ultrasonic energy through a bone-containing portion of a human or other animal disposed between the transducers, and circuitry for detecting an electrical signal generated by the receiving transducer in response to reception of ultrasonic energy. The transducers are disks of the copolymer supported by rigid rings spaced inwardly of their peripheries. A method of determining a characteristic of bone in a bone-containing portion of an animal includes positioning a pair of piezoelectric copolymer ultrasonic transducers respectively on opposite sides of, and ultrasonically coupling both transducers to, the animal portion, and transmitting ultrasonic energy through the animal portion including the bone to be tested from one transducer to the other. The animal portion may be a human heel.

3 Claims, 17 Drawing Sheets

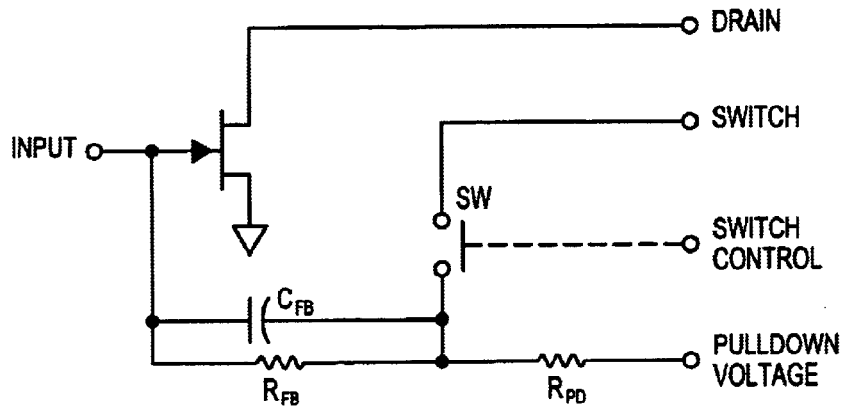
FIG. 18A - N-Channel FET Input Stage
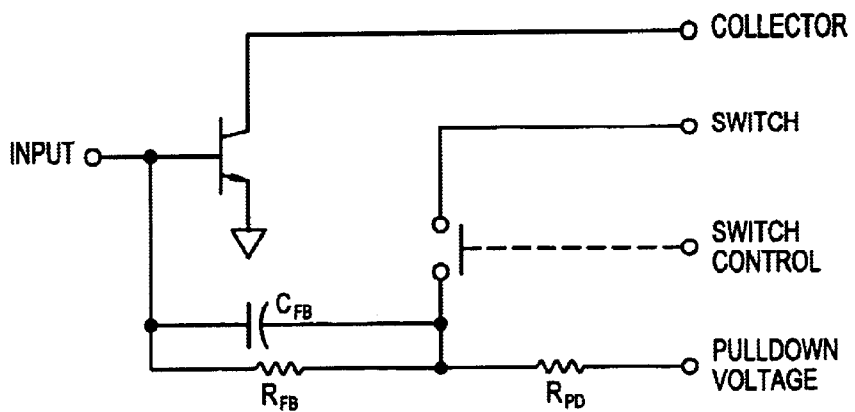
FIG. 18B - NPN Transistor Input Stage

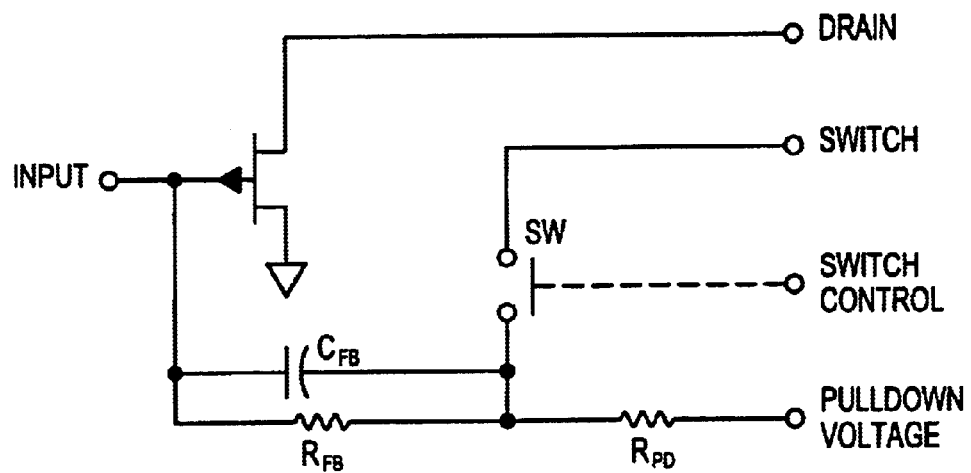
FIG. 18C - P-Channel FET Input Stage
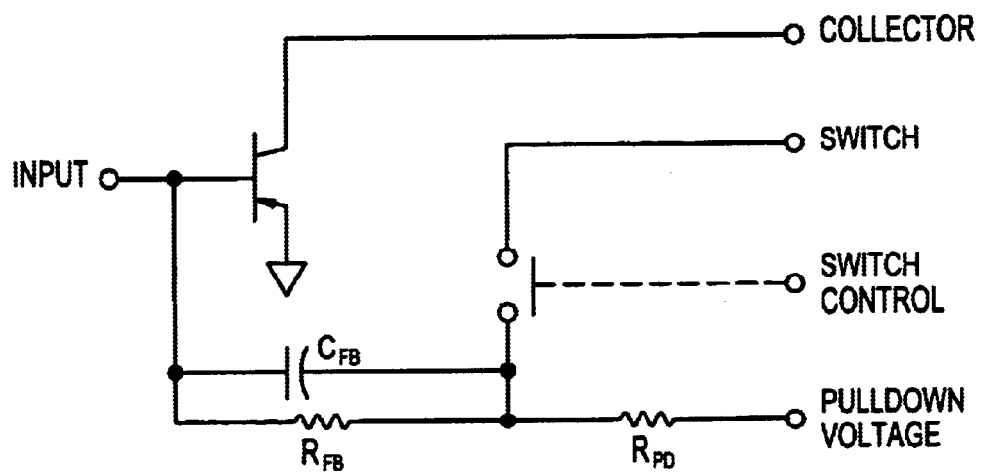
FIG. 18D - PNP Transistor Input Stage

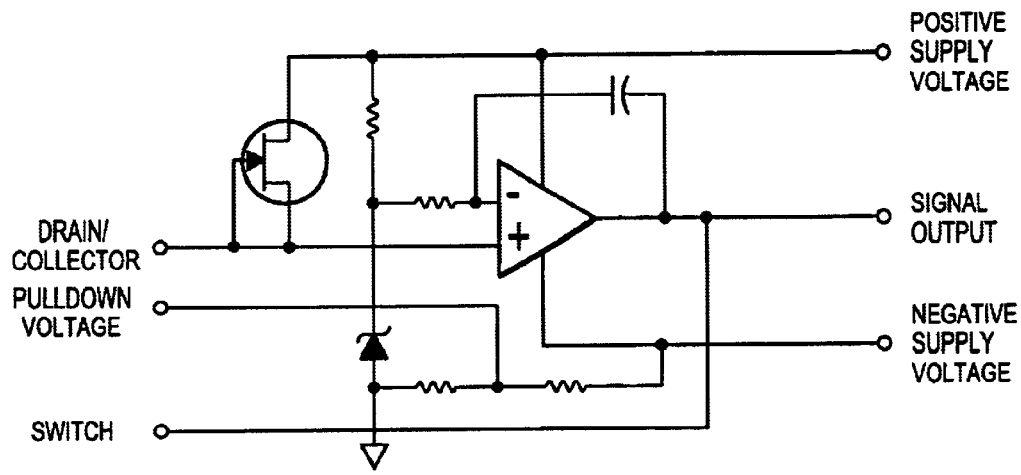
FIG. 18E - PREAMPLIFIER OUTPUT STAGE
For N-CHANNEL OR NPN INPUT STAGE
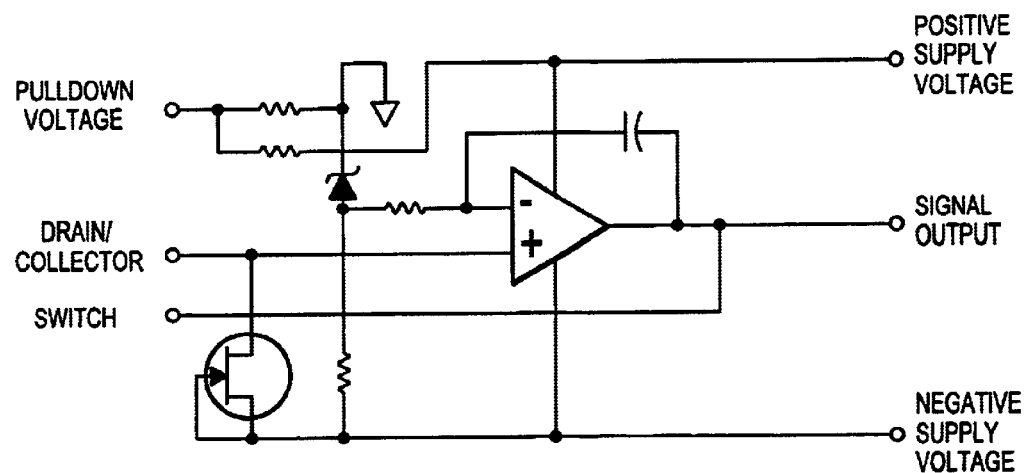
FIG. 18F - PREAMPLIFIER OUTPUT STAGE
For P-CHANNEL OR PNP INPUT STAGE

ULTRASONIC BONE TESTING WITH COPOLYMER TRANSDUCERS

CROSS REFERENCE TO RELATED APPLICATION

This application claims the priority benefit, under 35 U.S.C. §119(e)(1), of applicants' copending U.S. provisional application Ser. No. 60/140,638, filed Jun. 23, 1999, which is incorporated herein in its entirety by this reference.

BACKGROUND OF THE INVENTION

This invention relates to apparatus and methods for testing characteristics of animal bones, for example human bones, by transmitting ultrasonic energy through bone tissue to be tested.

The testing of bone tissue characteristics such as bone mineral density (BMD) in living humans is widely utilized in present-day medical practice to determine whether and to what extent a patient has osteoporosis or other bone disease. One convenient and effective way of testing bone tissue characteristics is by transmitting ultrasonic energy through a bone in a patient's limb or extremity, between ultrasonic transducers respectively disposed on opposite sides of the limb or extremity, while the transducers and bone-containing limb or extremity are stably held in stationary, predetermined relation to each other in a support or frame. It is currently preferred, in at least many instances, to perform ultrasonic testing on the heel bone (os calcis, or calcaneal bone), with the foot of the patient positioned in the support and the ultrasonic transducers facing each other on opposite sides of the heel.

For effective coupling of ultrasonic energy to the heel, some testing systems (wet systems) include a tank or container of liquid in which the foot is immersed, and which is in contact with the transducers. Dry systems have also been developed, in which a pair of pads constituted of a suitable polymer or filled with a liquid coupling medium such as a gel (the term "liquid" herein embracing gels) are respectively disposed between the heel and the two transducers, each pad being in contact with and somewhat compressed between its associated transducer and the heel.

The transducers employed are devices for converting electrical energy to ultrasonic energy and vice versa. Thus, one of the transducers is energized electrically to generate ultrasonic energy which is transmitted through the heel or other body portion containing the bone being tested and received by the other of the transducers. The receiving transducer in turn generates an electrical signal in response to the received ultrasonic energy which has traversed the bone. This electrical signal is detected by appropriate electrical circuitry and utilized in deriving a value representing, for example, the speed of sound (SOS) through the bone or broadband ultrasonic attenuation (BUA) by the bone. Such values can be correlated with medically significant bone characteristics such as BMD.

In conventional systems as heretofore known, each of the ultrasonic transducers which produce and receive the ultrasonic energy is typically a ceramic piezoelectric crystal heavily damped with a composite backing and/or tuned to obtain the desired broadband frequency response. These transducers are extremely labor-intensive to manufacture, requiring an extensive amount of machining, gluing and compressing in production. Because of the many manufacturing steps, the nature of the ceramic crystal and the damping backing, the final product is extremely variable in nature. This variability is manifested in frequency response, amplitude and ultrasonic wave shape.

SUMMARY OF THE INVENTION

The present invention, in a first aspect, broadly contemplates the provision of ultrasonic bone testing apparatus comprising a pair of ultrasonic transducers at least one of which comprises a piezoelectric copolymer; mounting structure supporting the transducers in facing spaced relation to each other, so as to be respectively positionable on opposite sides of and both coupled ultrasonically to an animal portion containing a bone, for respectively transmitting ultrasonic energy through and receiving ultrasonic energy transmitted through the animal portion including the bone; and electrical circuitry connected to the transducers to energize one transducer to transmit ultrasonic energy and to detect an electrical signal generated by the other transducer in response to received ultrasonic energy.

In this apparatus, the mounting structure may include a support for positioning the animal portion between the transducers, and a device for coupling the transducers ultrasonically to the animal portion. Preferably, both transducers are piezoelectric copolymer transducers. Each of the transducers typically or conveniently comprises a plate of a piezoelectric copolymer, the term "plate" being used herein to denote a generally flat element such as a sheet, slab or film, whether self-sustaining or coated on a substrate layer and/or itself provided with a protective or other coating. Alternatively, since the copolymer of the transducer is easily shaped, either or both of the copolymer transducers included in the present invention may have a curved surface, to provide focusing, and/or may be constituted as an array of multiple discrete copolymer transducer elements, such an array having advantages for correction for phase cancellation and/or for imaging; in such an array, the individual elements of the array could correspond to pixels and each pixel could have a different BUA, SOS or BMD value.

A currently preferred embodiment of the invention includes two copolymer transducers, respectively serving as a transmitter and a receiver of ultrasonic energy, and each comprising a copolymer disk having a periphery and two opposed major surfaces, one of which is disposed to face the bone-containing animal portion. In accordance with a particular feature of the invention, in this embodiment each such transducer further includes a rigid support structure, such as (for instance) a rigid ring, engaging the other major surface of the disk inwardly of the periphery thereof for supporting the disk against pressure exerted on the first-mentioned major surface of the disk. For example, in embodiments wherein the coupling device comprises a pair of polymer pads, each disposed in contact with one major surface of one of the transducers, and respectively engageable with opposed surface regions of an animal portion positioned in the support as aforesaid, the rigid support structure (e.g., ring) engaging the other major surface of each transducer disk inwardly of the periphery thereof supports the disk against pressure exerted on the disk through the last-mentioned pad.

In other embodiments, the coupling device includes a container for holding a body of a coupling fluid in which the animal portion is immersed when positioned by the support as aforesaid and with which the transducers are in ultrasonic energy transmitting contact.

Any of these embodiments may be arranged for use in testing procedures in which the animal portion is a human heel, the support being configured and dimensioned to position the heel, and the transducers and coupling device being disposed, SQ that ultrasonic energy transmitted from one transducer to the other transducer passes through the calcaneal bone of the heel.

The electrical circuitry may be arranged to use the detected electrical signal in deriving a value representative of the speed of sound through the bone through which the ultrasonic energy is transmitted as aforesaid. Alternatively, or additionally, the circuitry may be arranged to use the detected electrical signal in deriving a value representative of broadband ultrasonic attenuation (BUA) in the bone.

In a second aspect, the invention contemplates the provision of a method of determining a characteristic of a bone in a bone-containing portion of an animal comprising disposing a pair of ultrasonic transducers at least one of which comprises a piezoelectric copolymer respectively on opposite sides of, and ultrasonically coupling both transducers to, a bone-containing animal portion; electrically energizing one transducer to transmit ultrasonic energy through the animal portion including the bone, such that the transmitted ultrasonic energy is received and converted to an electrical signal by the other transducer; detecting the electrical signal; and using the detected signal to derive a value representative of the bone characteristic to be determined. Again, in embodiments wherein the transducers so used are disks of a piezoelectric copolymer, each having a periphery and opposed major surfaces, one of which is oriented to face the animal portion, the method of the invention further includes the feature of supporting the other major surface of each disk by disposing, in contact therewith, rigid support structure spaced inwardly from the disk periphery.

In the apparatus and method of the invention, the use of piezoelectric copolymer disks as transducers affords significant economies, as well as effective performance. The piezoelectric copolymer material requires fewer manufacturing steps and is less variable in ultrasonic properties than conventional ceramic piezoelectric transducers; hence the use of this material enables a more uniform product to be manufactured. The provision of the rigid support structure, spaced inwardly of the periphery of the copolymer disk, enables such use of these relatively deformable and/or frangible thin disks without distortion or breakage.

Further features and advantages of the invention will be apparent from the detailed description hereinbelow set forth, together with the accompanying drawings.

BRIEF DESCRIPTION OF THE DRAWINGS

FIGS. 18A, 18B, 18C, 18D, 18E and 18F of array detector circuitry for use with the receiver of FIGS. 17A and 17B.

DETAILED DESCRIPTION

The invention will be described in detail, for purposes of illustration, as embodied in apparatus and methods for testing the calcaneal (heel) bone of living human subjects or patients, including both dry and wet systems, such embodiments representing currently especially preferred practice. In a broader sense, however, the invention is not limited thereto, but may be employed e.g. to measure SOS and/or BUA to test other bones in other portions (e.g., limbs or extremities) of the human body, and to test bones of living animals other than humans.

Dry System

An embodiment of the apparatus of the invention may be incorporated in a dry system for ultrasonic bone testing, generally of the type set forth in U.S. Pat. No. 5,755,228 and in U.S. patent application Ser. No. 08/477,580 filed Jun. 7, 1995 (now U.S. Pat. No. 6,004,272), Ser. No. 08/866,804 filed May 30, 1997 (now U.S. Pat. No. 5,935,073), and Ser. No. 09/277,838 filed Mar. 26, 1999 (which also describes wet systems for ultrasonic bone testing) (now U.S. Pat. No.

6,352,512 B1), the entire disclosures of which are incorporated herein by this reference.

Such a system, now to be described, is shown in FIGS. 1–5. As set forth in the aforesaid application, with reference to FIG. 1, the dry-type ultrasonic bone analysis apparatus there illustrated combines the mechanisms to position and restrain the foot and lower leg into a single foot restraint device 1. The foot restraint device 1 comprises two assemblies, a shin guide assembly 2 and a foot well assembly 3.

Figure 2:
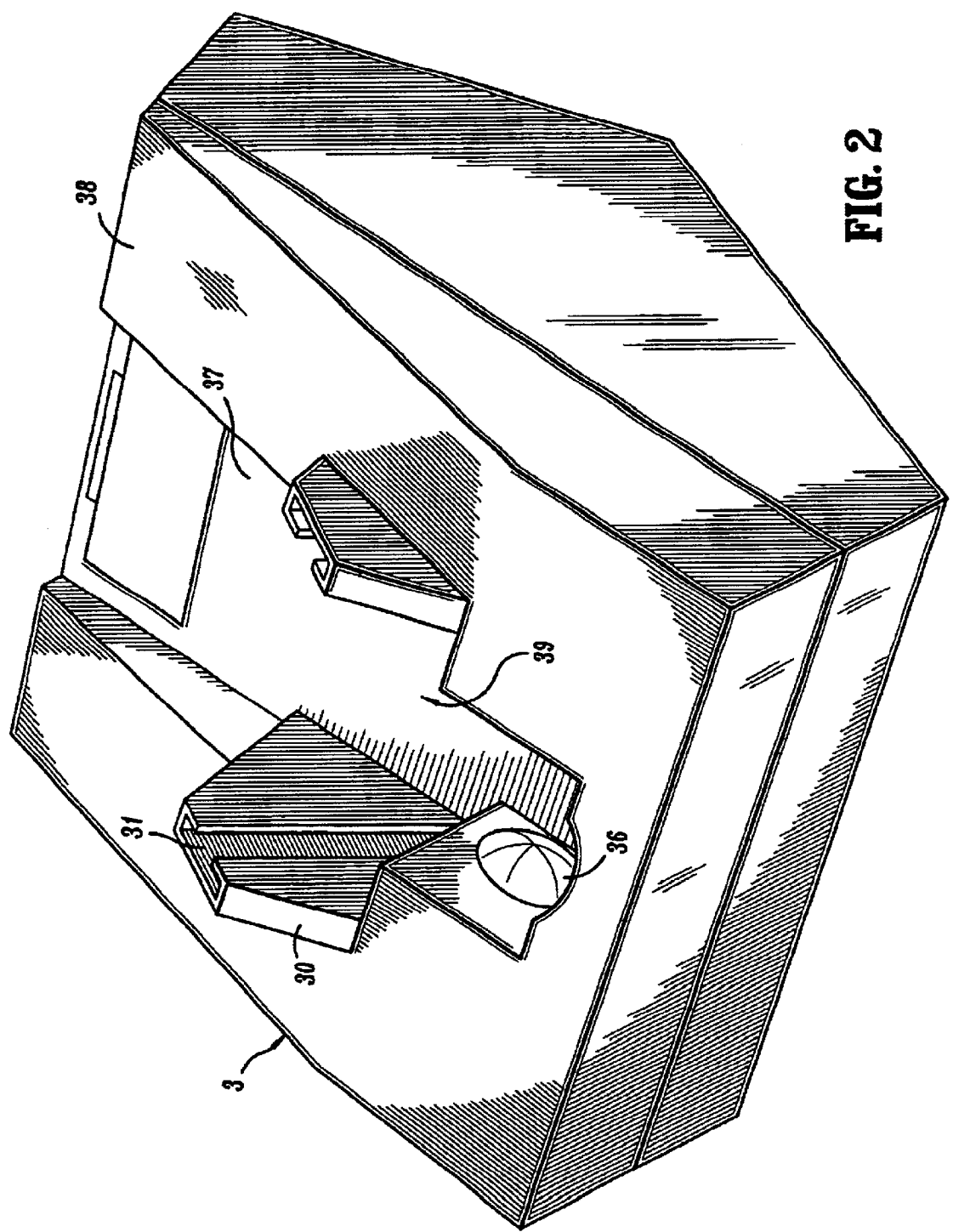
FIG. 2 is a perspective view of a foot well assembly of the apparatus of FIG. 1.

As seen in FIG. 2, the foot well assembly 3 comprises a box cover 38 having a foot support 39, and foot well bottom 37. The foot support 39 has an area slightly larger than a human foot such that even a large foot can fit comfortably.

Transducer ports 36 are located on the sides of the foot support 39, towards the rear.

Referring back to FIG. 1, the shin guide assembly 2 includes a plastic molded form 20 lined with contoured foam lining 41. The molded form 20 is a combination of restraints for the shin, instep, and front of the foot into a single piece.

Figure 1:
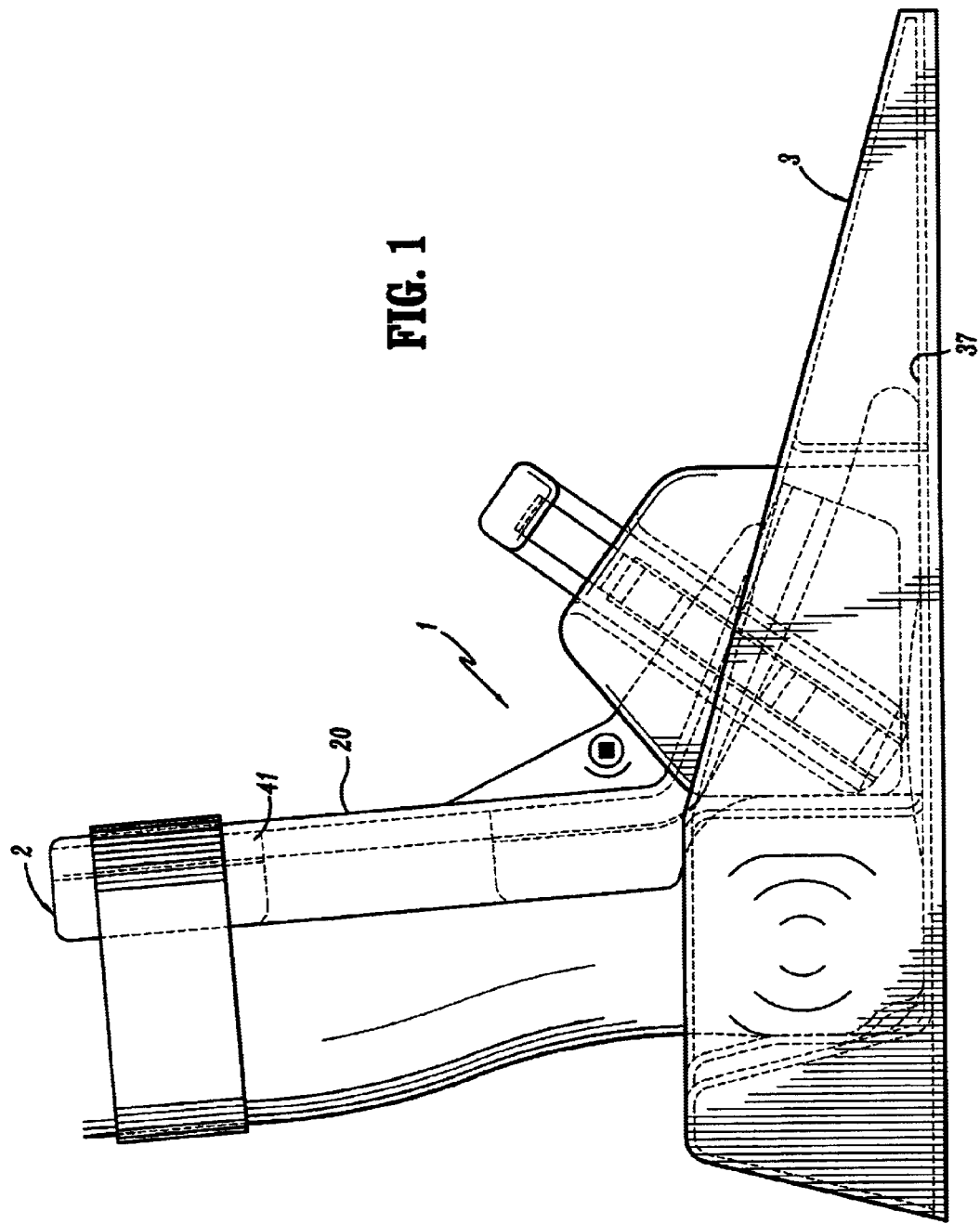
FIG. 1 is a side view of a foot restraint assembly of a first dry system type of ultrasonic bone testing apparatus in which the present invention may be embodied in an illustrative form.
Figure 3:
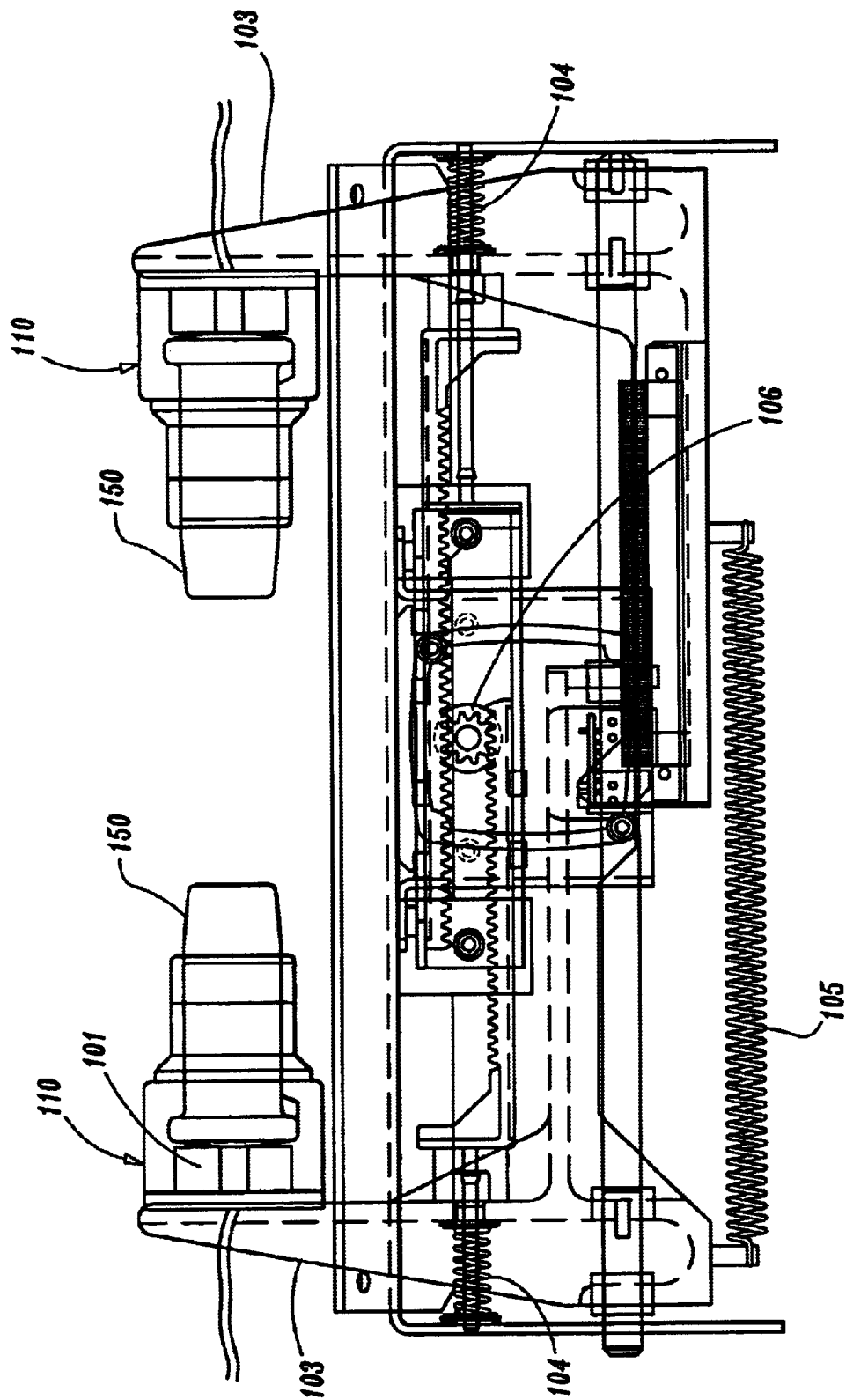
FIG. 3 is a sectional view of a transducer drive mechanism of the apparatus of FIG. 1.

Referring now to FIG. 3, the transducer drive mechanism of the apparatus of FIG. 1 includes a pair of transducer assemblies 110. The transducer assembly 110 includes transducer 101 and acoustical coupling pad 150, as hereinafter further described.

In this structure, the repeatable coupling of the transducers to the foot is accomplished by the specially shaped delay lines constituted by the coupling pads 150 that conform to the shape of the heel. The acoustical delay line also allows the transducer's wavefronts to evolve from the granular near field pattern to a smoother far field pattern before entering the foot. The acoustical and mechanical properties of the elastomer coupling pad are inherently critical to the operation of the described apparatus.

The transducers 101 are mounted to respective carriages 103 that slide along a lateral-medial axis. Respective compression springs 104 attached to the carriages 103 apply opposing lateral forces towards the center of the foot. The carriage/spring assembly is free floating and will center itself on the foot with approximately equal pressure on both sides.

An extension spring 105 applies the initial pressure when the coupling pads 150 reach the patient's foot. To adjust the pressure in small increments, a stepper motor with rack and pinion mechanism 106 will move a finite number of steps and compress the compression springs 104 that are attached to the respective carriages 103. The compression springs 104 will pull the respective transducers 101 and pads 150 inward at a force proportional to the spring rate and distance translated.

Figure 4B:
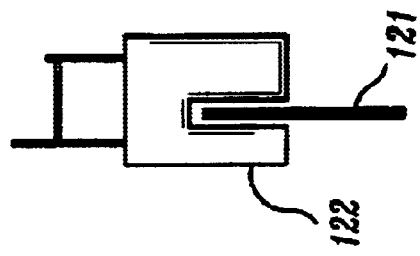
FIGS. 4A and 4B are front and side views of a position encoder of the apparatus of FIG. 1.
Figure 4A:
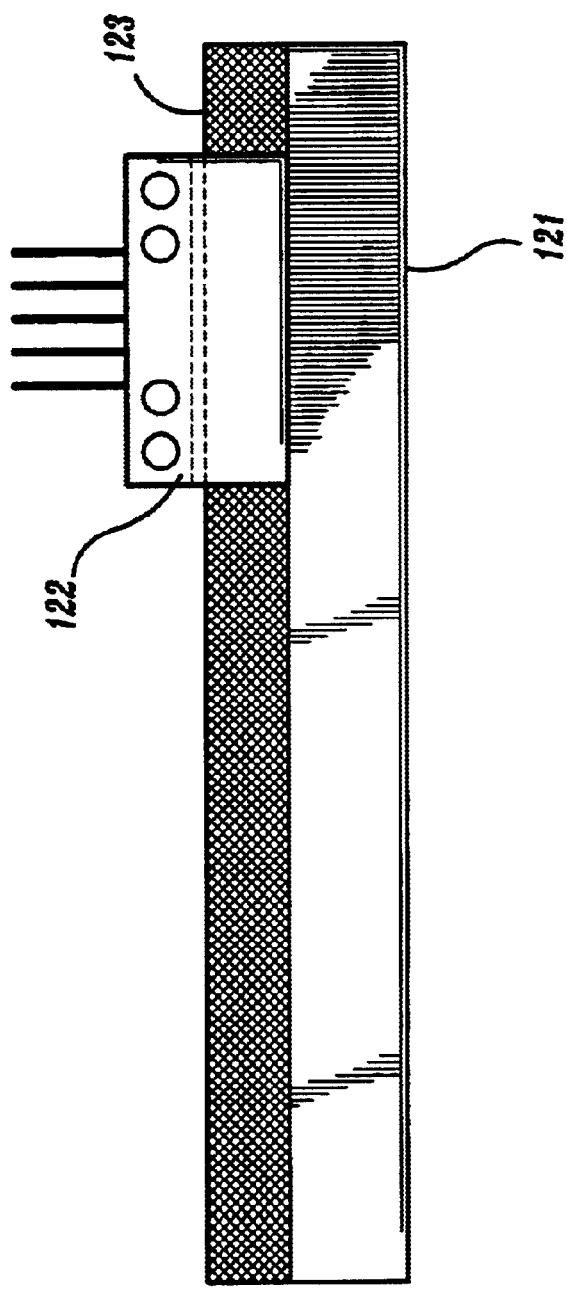
Figure 5:
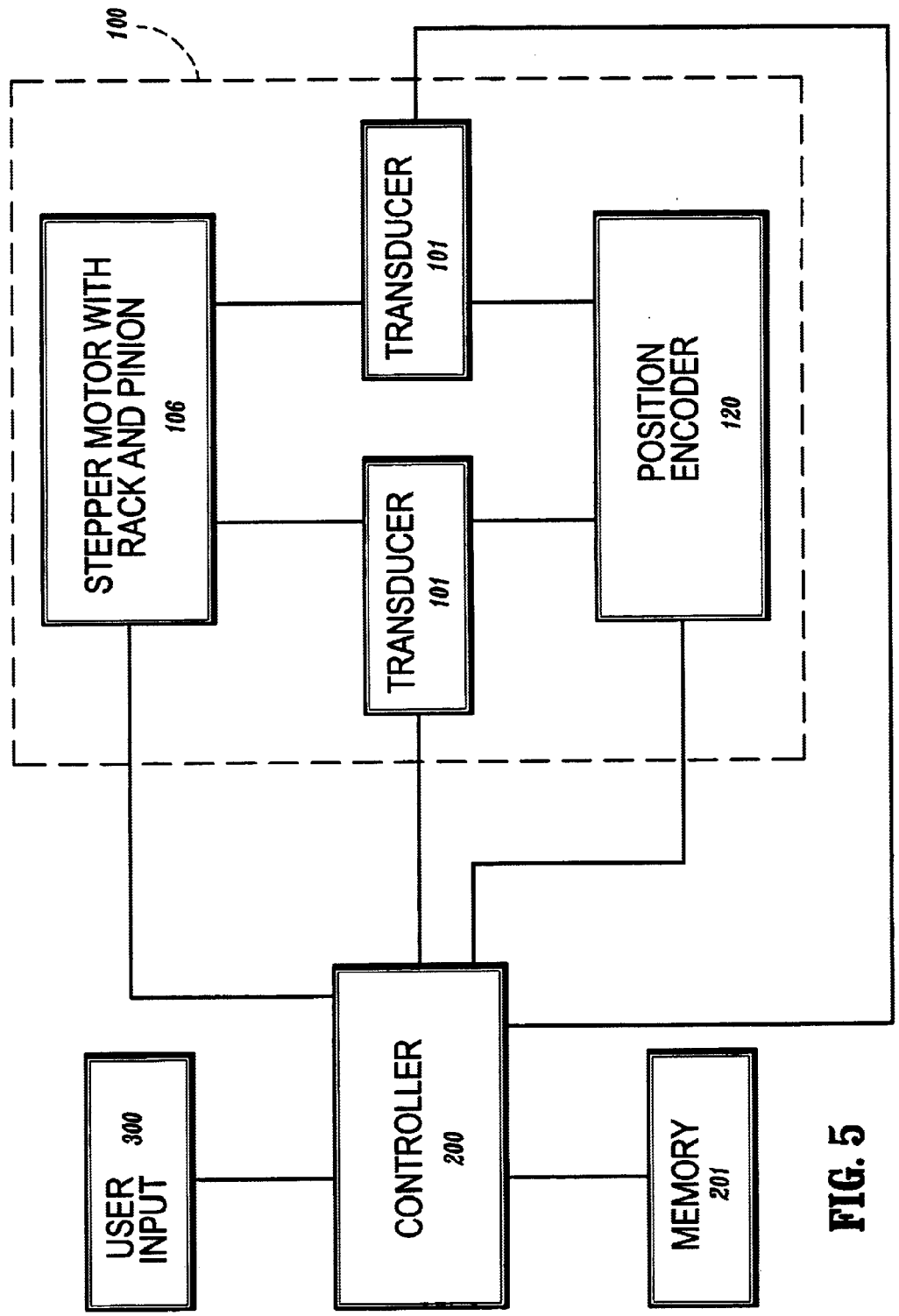
FIG. 5 is a block diagram showing automatic positioning by a transducer drive mechanism of the apparatus of FIG. 1.

The distance between the transducers 101 is continuously measured by means of a position encoder 120 that is mechanically linked to the motion of the transducers 101. Referring to FIGS. 4A and 4B, front and side views of the position encoder 120, respectively, a preferred encoder uses a code strip 121 mounted onto one of the carriages 103 along with an optical encoder reader 122 mounted on the other of the carriages 103. As the distance between the transducers 101 changes, the code strip 121 moves between the slot of the optical encoder reader 122, and the optical reader 122 reads lines 123 of the code strip 121 as the lines 123 are traversed.

The transducer drive mechanism 100 automatically positions transducer assemblies 110 against the patient's heel with sufficient pressure to insure ultrasonic coupling. The controller 200 is preferably a microprocessor-based controller having memory 201 (e.g. RAM and ROM) for storing system and application software and input/output circuitry. The controller 200 controls the operations of the stepper motor 106 according to the program stored in its memory and the positional data supplied by the position encoder 120. Accordingly, the transducer drive mechanism 100 under the control of the controller 200 provides automatic positioning.

The transmitter circuit located in the controller 200 applies pulses to the transmitter transducer 101. Response signals received by the receiving transducer 101 are amplified, digitized and supplied to controller 200. Using these digitized signals and information from the position encoder 120, the controller 200 determines parameters of interest, including broadband ultrasound attenuation and bone velocity. Also, the controller 200 calculates a speed of the ultrasonic signals through the foot using the distance between the transducers determined by the position encoder 120. An apparatus for measuring bone characteristics by means of ultrasound is well-known in the art. Such an apparatus is disclosed for example in U.S. Pat. No. 4,774,959 issued to Palmer et al. on Oct. 4, 1988 which is incorporated herein by this reference.

The controller 200 calculates a temperature from the velocity of sound through the pad material. The temperature thus calculated is used to correct for temperature dependent inaccuracy in the ultrasound measurement. For example, the controller 200 applies a temperature dependent term to correct for the broadband ultrasound attenuation through the coupling pads 150. Furthermore, the controller 200 uses the temperature calculated to determine if the apparatus is operating within the specified environmental range allowed, and if not, the operator is informed that the apparatus is not ready to be used.

In addition, guided by operator input 300, the following are examples of additional selectable functions provided by the transducer drive mechanism 100 under the control of controller 200 and its stored program: (1) separate the transducers 101 to allow the foot to be moved to and from a position between the transducers 101 without interference from the transducers; (2) move the position encoder 120 to a known transducer separation; (3) extend the transducers 101 to a cleaning or standby position; and (4) bring the transducer pads 150 into contact with one another for initialization. The operator input 300 can be any one of the conventional input devices such as pre-allocated buttons, keyboard/keypad device, etc.

Several features of the coupling pads 150 are important to the operation of the described invention. The acoustic impedance of the material of the pads 150 is matched to the acoustic impedance of human skin to provide a minimal loss of power and reduce extraneous reflections. Further, the SOS of the pads is close to the SOS of the heel so as to provide minimal error in the SOS measurement. Preferably, the coupling pads are elastomer coupling pads.

The coupling pads 150 also provide a waveguide function for the acoustic beam providing a sufficient distance along the propagation axis to allow the wavefronts to evolve into a more uniform intensity pattern. To this end, the aforementioned acoustical delay lines are provided by the pads 150 to allow the wavefronts to evolve from the granular near field pattern to a smoother far field pattern before entering the foot.

The pads 150 are chosen to have a durometer corresponding to a sufficiently flexible waveguide that can partially conform to the shape of a foot without discomfort to the patient. The shape of the pads 150 conforms to the heel to eliminate any gaps between the foot and pad.

Figure 6:
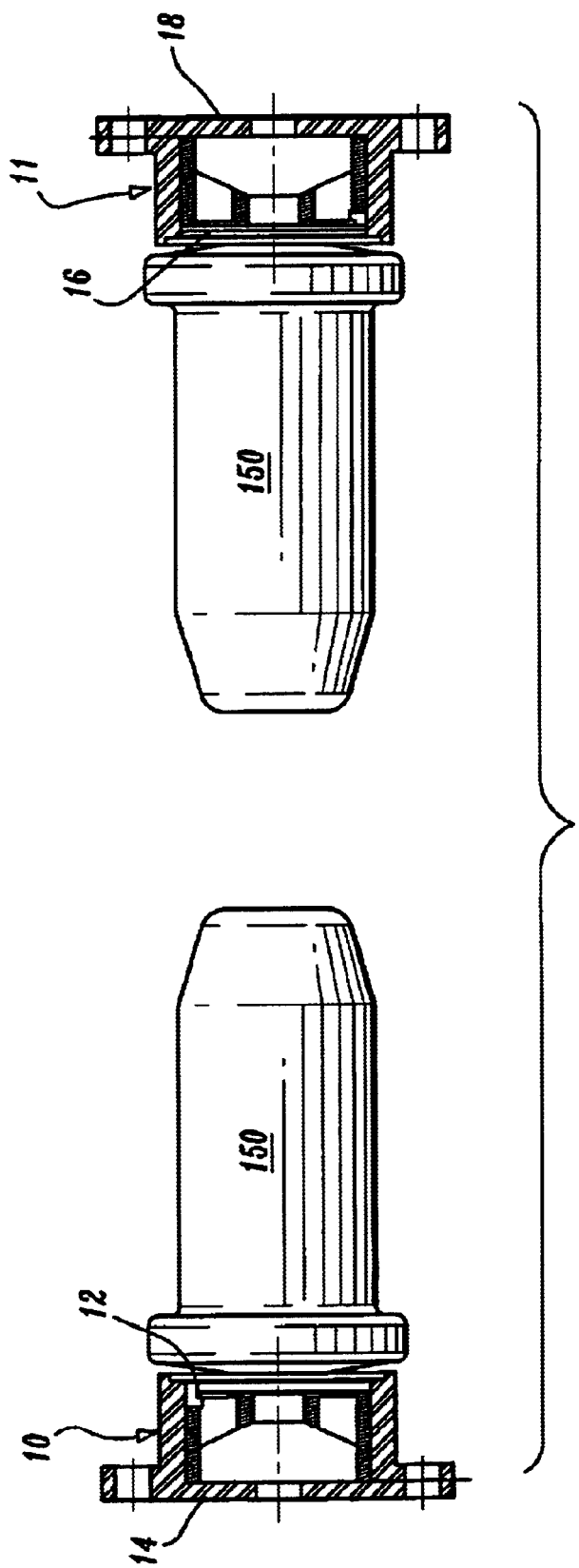
FIG. 6 is a view of the pads and copolymer transducers of an embodiment of the invention incorporated in the system of FIG. 1.

The coupling pads 150 are illustrated in FIGS. 3 and 6. The surface of the pad that contacts the patient's skin is shaped to expel air bubbles from the contact area when pressure is applied. In addition, in currently preferred embodiments of the unit 150 of FIGS. 3 and 6, the shoulder for holding the pad is located at the slightly convex end of unit 150 proximal to the transducer.

The material of the coupling pad is required to be compatible with coupling gel and non-irritating to the skin. One preferred material is Ciba-Geigy polyurethane (TDT 178-34) mixed with an additive to provide a cured durometer of approximately 12 to 18 Shore A.

While the elastomer coupling pad is preferred, the coupling pads may be a homogeneous material, a gel pad, or a liquid or gel-filled bladder. The shape of the bladder may be conical whereby air bubbles are expelled when the pad engages the heel.

In a known system, commercially available coupling gel is commonly used between the skin and coupling pads. The commercially available coupling gel is typically water-based. While such water-based gels can be used, a non-aqueous jelly is preferred in this invention. One implementation of the invention uses petroleum jelly which has been processed to eliminate air bubbles as a coupling gel.

In the operation of the apparatus, a method of calibration may be employed which measures an ultrasonic signal transmitted through the coupling pads while the pads are mutually in contact, the measurement being relatively close in time to a measurement of a signal passing through a heel or a phantom interposed between the pads. The received signal passing through the mutually touching pads may be used as a reference for a BUA measurement. A measurement of a propagation time of the ultrasonic signal through the mutually touching pads may be used as a reference time for comparison to the signal passing through the heel, and thereby used for calculating a time of propagation through the heel. Because proximity in time is accompanied, presumptively, by proximity in ambient temperatures for the respective measurements, no correction for time or temperature drift between the measurements is required.

In order to assess a bone characteristic such as BMD by speed of sound (SOS) measurement in the apparatus of FIGS. 1–5, it is necessary to measure accurately the SOS of the body part (heel) through which ultrasonic energy is transmitted while obtaining adequate ultrasonic contact between the heel and the transducer pads, maintaining patient comfort, and allowing for the fact that human body parts are irregularly shaped.

The $SOS_p$ of a body part (e.g., a human heel) is given by $$SOS_p = w/t$$

where w is the width of the body part and t is the time it takes the ultrasound to pass through the body part. Error in the measurement of $SOS_p$ can come from incorrectly measuring w or t. To measure t accurately, the procedure just described for determining a reference time using mutually touching pads may be employed, just before the heel is inserted between the pads. The difference in time for the measurement with the pads touching and the foot inserted between the transducer pads is used to estimate t.

Measurement of w presents problems owing to considerations of pad squish, i.e., the distance a pad is compressed when pressure is applied to it. If the transducer pads are not very stiff, the estimate of w may be significantly inaccurate. A typical heel is 33 mm wide; squishing of the pad by 1 mm, without compensation in the calculations, will produce an error in $SOS_p$ of $\frac{1}{33} = 3.3\%$, which is a very large error, since the full biological range of variation in $SOS_p$ is on the order of 10%, and accuracies on the order of 0.3% are desired. Stiff transducer pads, however, cannot conform very well to the human heel and do not in general provide adequate ultrasonic coupling for BUA measurements (which are commonly desired when evaluating bone). Moreover, significant pressure is needed to provide ultrasonic coupling, and a hard transducer pad can cause significant patient discomfort with possible complications such as bruises.

Attempts to control the amount of squish by careful control of the amount of pressure applied to the heel are hampered by the irregularity of the heel shape and the difficulty of controlling the durometer of any polymer to sufficient tolerance. Moreover, if the durometer of the transducer pad changes with age and/or temperature (as commonly occurs), the amount of squish will vary notwithstanding control of applied pressure.

A procedure for circumventing these problems includes, as an initial step, bringing the transducer pads into contact with each other, transmitting ultrasound between the transducers, measuring the propagation time $t_0$, and at the same time recording the distance do between the two transducer faces (not the distance between the pads). Then, the patient's heel is inserted in the apparatus, ultrasound is again transmitted, the propagation time $t_1$ of the ultrasound is measured, and the distance $d_1$ between the transducer faces with the heel inserted is measured. A value SOS' can then be determined from the relation $$SOS' = w'/t'$$

where w' is the difference $d_1 - d_0$, between the intertransducer distances measured when the heel is inserted and when the pads are touching each other, and t' is the difference $t_1 - t_0$.

It will be appreciated that w' is not the same as the width w of the foot, because it includes the different amount of squish when the pads are touching each other and when they are against the heel. Moreover, t' is not the same as the time t of ultrasound propagation through the foot because the sound may travel a greater or lesser distance if the amount of squish is different in the two measurements. The relation of w' to w can be expressed by $$w' = w(1 + \delta)$$

where $\delta$ is the difference between the amount of squish when the pads touch each other and when the heel is between them, divided by the width w of the heel. For all practical cases, $\delta << 1$. The relation of t' to t is given by $$t' = t(1 + \epsilon)$$

where $$\epsilon = (w\delta/SOS_{pads})/t$$

The numerator ($w\delta/SOS_{pads}$) is the difference in squish of the two measurements (with the pads touching each other and with the heel between them) divided by the speed of sound through the transducer pad material; this gives the extra time taken because of the greater or lesser squish of the two pads in the two measurements. In all practical cases, the numerator is much smaller than the denominator because the time of ultrasound travel through the body portion (heel) is much greater than the time through the difference in pad squish; hence $\epsilon \ll 1$.

From the foregoing, $$SOS' = w'/t' = (w/t)(1+\delta)/(1+\epsilon)$$

and since $\epsilon \ll 1$, this equation can be expanded as a power series, substituting $SOS_p$ (the quantity to be measured) for $(w/t)$:

$$SOS' = SOS_p\{1+\delta\}\{1-\epsilon+o^2(\epsilon)\}$$

$$= SOS_p\{1+\delta-\epsilon+o^2(\epsilon)\}$$

or, writing $\epsilon$ in terms of $\delta$, as defined above, $$SOS' = SOS_p\{1-(w\delta/SOS_{pads})/t)+\delta+o^2(\delta)\}$$

$$= SOS_p\{1+\delta(1-SOS_p/SOS_{pads})+o^2(\delta)\}$$

To estimate how accurately SOS' estimates $SOS_p$, it is only necessary to look at the first term (which is largest). As noted, $\delta$ is very small because it is the difference between the squish of the pads when they touch and when they contact the heel, so that if the total squish of the pads is about 1 mm (as in the example given above), the difference in squish is much less, e.g., perhaps 0.5 mm, so that $\delta = 0.5/33 = 0.015$. There is a self-adjustment in that if the durometer of the pads changes with age or temperature, the pads will squish to a greater or lesser extent on both measurements, hardly affecting the difference in squish. Moreover, the error in $SOS_p$ estimate varies not as $\delta$ but as $\delta(1-SOS_p/SOS_{pads})$; thus, if the transducer pads are made of a material chosen such that $SOS_p \approx SOS_{pads}$, the error is very small. Of course, since body parts have a range of $SOS_p$ (between about 1450 and about 1670 m/s), it is impossible to select one pad material that matches all $SOS_p$, but if the pad material is so chosen that $SOS_{pads}$ is approximately in the middle of the biological range (an example is Ciba-Geigy elastomer TDT 178-34), then $(1-SOS_p/SOS_{pads})$ is slightly more than 0.07 in the worst case, and will usually be much smaller. Therefore, SOS' will differ from $SOS_p$ in the worst case by only about 0.015×0.07 or 0.105%, which affords an acceptable accuracy of estimation of $SOS_p$ by determination of SOS'.

Copolymer Transducers

The apparatus as thus far described is substantially the same as that shown in the aforementioned U.S. Pat. No. 5,755,228 and U.S. patent application Ser. No. 08/477,580. Heretofore, however, the transducers ordinarily employed in such apparatus have utilized ceramic piezoelectric crystals as active transducer elements. In contrast, as a particular feature of the present invention, in the embodiment now to be further described with reference to FIGS. 6–13, the transducers 101 are copolymer transducers, viz., a copolymer transmitter transducer 10 and a copolymer receiver transducer 11, respectively associated with two integral pad/delay units 150 as illustrated in FIG. 6.

Figure 7A:
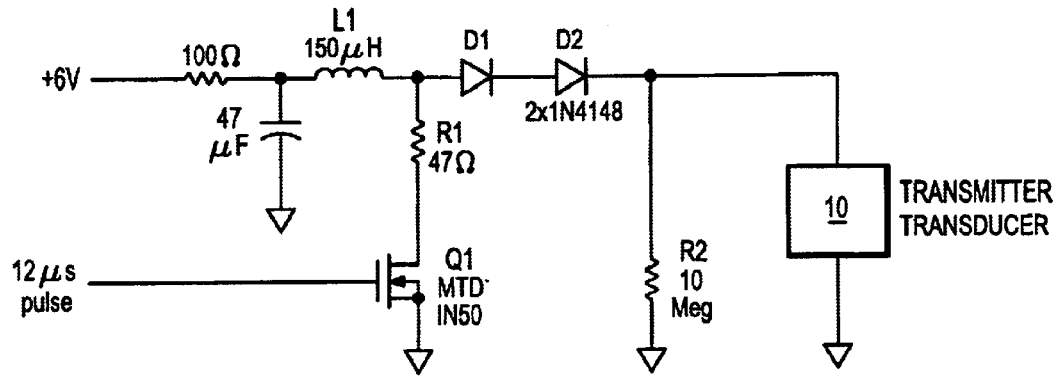
FIGS. 7A and 7B are diagrams of the transmitter circuit and receiver circuit, respectively, of the last-mentioned embodiment of the invention.
Figure 7B:
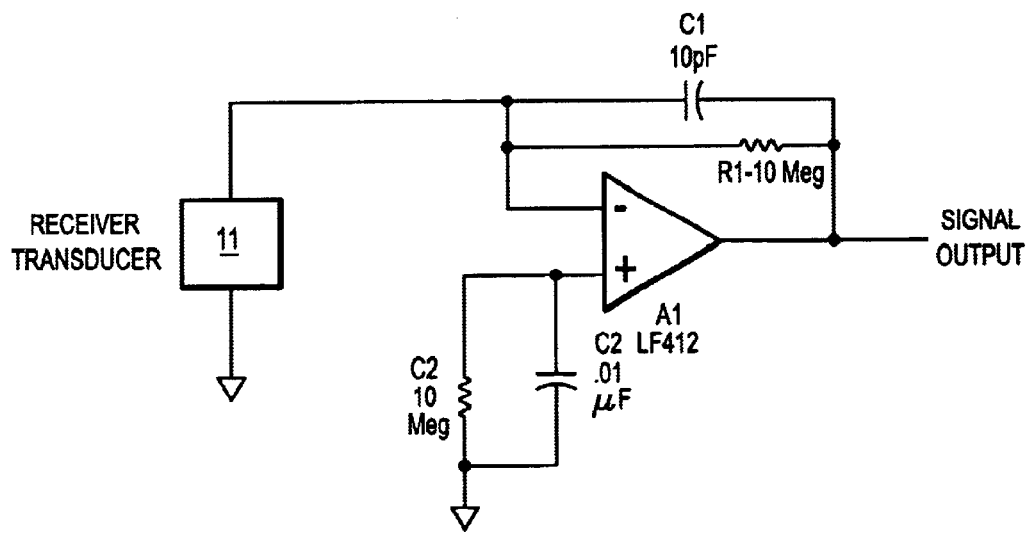

Illustrative, experimental circuits for the copolymer transmitter transducer and the copolymer receiver transducer, in the described embodiment of the invention, are respectively shown in FIGS. 7A and 7B.

The following is a description of these experimental circuits respectively used for driving a copolymer ultrasound transmitter transducer and for conditioning the electrical signals generated by an ultrasound receiver transducer.

TRANSMITTER CIRCUIT—The transmitter circuitry (FIG. 7A) consists primarily of an inductor L1, resistors R1 and R2, a switching transistor Q1, and a number of high speed controlled avalanche diodes D1 through Dn. The number of diodes needed is determined by the voltage it is desired to apply to the transducer and by the voltage rating of the individual diodes. The circuit requires a well regulated and well filtered DC supply voltage and an electrical pulse signal suitable for switching on and off the transistor Q1.

A preferred implementation of the circuit is shown schematically in FIG. 7A. Immediately preceding the desired application of a transmitter pulse a pulse is applied to the gate to make transistor Q1 conductive for a period of approximately 12 microseconds. During this pulse the current through L1, R1 and Q1 increases and approaches asymptotically a current determined by the supply voltage and the resistance of the circuit, primarily resistor R1. At the conclusion of the 12 microsecond pulse transistor Q1 suddenly ceases to conduct. Inductor L1 forces the current through the inductor to continue to flow for a brief period of time. Since the current cannot flow through transistor Q1 it flows into the capacitance at the junction of resistor R1 and inductor L1, primarily through diodes D1 and D2, to the capacitance of the transmitter transducer. The current flowing into this capacitance causes the voltage across the transducer to rise and the voltage thus applied to the inductor causes the current in the inductor to decrease. When this current has decreased to zero the voltage across the transducer ceases to increase. Diodes D1 and D2 prevent the charge on the transducer from flowing back out through the inductor. The transducer charge, instead, is drained gradually through resistor R2 which is of sufficiently great resistance not to affect the amplitude of the pulse significantly for several tens of microseconds but eventually allows the transducer voltage to decay to a negligible value before the next following pulse is desired.

The voltage to which the transmitter transducer is charged is determined by the transducer capacitance, the inductance L1, and the current to which inductor L1 is charged. If the inductor is charged to a current $I_L$ the energy stored in the inductor is equal to one-half of L1 times the square of $I_L$. In the course of the pulse this energy is transferred fully (except for certain small but inevitable losses due to the inefficiency of the circuit) to the capacitance of the transducer, which is primarily a capacitive device. The energy stored in a capacitor is equal to one-half of the capacitance times the square of the capacitor voltage. Therefore, the voltage across the transducer at the peak of the pulse is equal to the inductor charging current times the square root of the ratio between the inductance and the transducer capacitance.

The time required for the voltage across the transducer to increase from its baseline level to the peak is determined by the resonant frequency of the inductance with the transducer capacitance and is equal to one half the cycle time of this frequency.

For the preferred circuit shown in the figure and a transducer capacitance of 150 picofarad the peak transducer voltage is calculated to be 128 volts. The time from the base to the peak of the pulse is calculated to be 0.47 microsecond. This corresponds to a conventional rise time (10% to 90%) of approximately 0.28 microsecond.

RECEIVER CIRCUIT—The receiver circuit conditions the charge pulse generated by the receiver transducer in response to an ultrasound signal. The preferred circuit shown in FIG. 7B consists of an operational amplifier A1, a feedback capacitor C1, a feedback resistor R1, an input resistor R2, and a bypass capacitor C2. The operational amplifier requires a DC power supply of both a positive and a negative voltage such as +/−8 volt or +/−15 volt. The DC power supply leads of the amplifier should be bypassed to ground in accordance with good engineering practice.

Matching the impedance of the transducer, which is capacitive, the amplifier feedback is also primarily capacitive. The 10 megohm feedback resistor provides a baseline at ground potential. The feedback at the signal frequencies of interest is provided primarily by the 10 picofarad feedback capacitor. The transducer is connected to the inverting input of the amplifier. The amplifier's non-inverting input is grounded through a 10 megohm input resistor which compensates for the common mode input current. This resistor is bypassed by a 0.01 microfarad bypass capacitor to minimize noise in accordance with good engineering practice.

The amplifier output signal is proportional to the signal charge. The effective gain of the circuit is equal to the ratio of the transducer capacitance over the feedback capacitance. For example, the circuit shown in the figure provides a gain of 15 if the transducer capacitance is equal to 150 picofarad. The noise contributed by the amplifier circuit is kept to a minimum by using a high value (10 megohm) feedback resistor. If a signal proportional to the signal current is preferred, a differentiator (designed in accordance with good engineering practice) may be provided in subsequent processing circuits (not shown).

The active transducer element of the transmitter transducer 10 is a plate in the shape of a disk 12 comprising one or more layers of a piezoelectric copolymer. The disk 12 is mounted in a shallow, cylindrical, cup-shaped, rigid molded plastic housing 14 so as to extend, in the manner of a diaphragm, across the open end of the housing. Similarly, the active transducer element of the receiver transducer 11 is a plate in the shape of a disk 16 comprising one or more layers of a piezoelectric polymer, mounted in like manner at the open end of a shallow, cylindrical, cup-shaped rigid molded plastic housing 18.

The two housings 14 and 18 may in turn be mounted in the apparatus of FIGS. 1–6, in the manner illustrated in FIG. 3, with the two disks 12 and 16 facing each other in spaced-apart relation for interposition of a patient's heel therebetween. The slightly convex proximal ends of the two pad units 150 are respectively in contact with the transmitter and receiver disks 12 and 16, and, as further shown in FIG. 6, the pads 150 project therefrom toward each other for engaging opposite side portions of a patient's heel inserted between them. Thereby, the pad units 150 couple the transmitter and receiver transducers 10 and 11 ultrasonically to the heel so that ultrasonic energy generated by the transmitter transducer passes through the calcaneal bone of the heel and, after such traverse, is received by the receiver transducer.

The slight convexity of the pad ends proximal to the transducers serves to exclude bubbles of air, which would otherwise affect the measurements made by the apparatus. A gel such as petroleum jelly (pretreated by melting and resolidification for removal of bubbles from the jelly) is placed between the transducer and the slightly convex pad end.

The copolymers employed in the transducers are copolymers of vinylidene fluoride and trifluoroethylene, i.e., poly (vinylidene fluoride-trifluoroethylene) copolymers, hereinafter designated P(VDF-TrFE), in sheet form, wherein the mole t ratio of vinylidene fluoride to trifluoroethylene is between about 60/40 and about 90/10. Currently preferred are such copolymers having an electromagnetic coupling coefficient $k_t$ of between about 0.20 and about 0.30. P(VDF-TrFE) copolymers can be used in transducers in methods and apparatus within the broad scope of the invention, not only as piezoelectric materials but also as electrostrictive materials.

An illustrative but non-limiting specific example of a transmitter transducer 10 is shown in FIGS. 9A–9D. The piezoelectric polymer employed in this transducer is poly (vinylidene fluoride-trifluoethylene) copolymer (in a weight ratio of 75/25), hereinafter sometimes referred to as "P(VDF-TrFE) (75/25) copolymer." In this transducer, the housing is constituted of an outer cup member 14a and an inner sleeve 14b, both of which are rigid molded plastic elements, with a strain relief feature 14c. The periphery of the transducer disk 12 overlies the outer edge of the sleeve 14b and is secured by a potted seal 14d to the rim of the cup member 14a.

The disk 12 is a laminate of two layers 26, 28 of the P(VDF-TrFE) (75/25) copolymer, each 230 μm (9 mils) thick, bonded together by a 1 mil thick layer 34 of epoxy. On its outwardly facing (front) surface, the disk also includes a 10 mil front layer 44 of polycarbonate laminated by a 1 mil layer 46 of epoxy to a 12 mil layer 48 of aluminum. A 5 mil shield electrode layer 52 of silver ink overlies the outer surface of the outer layer 26 of the copolymer and extends around the peripheral edge of the two copolymer layers; the aluminum layer 48 is bonded to this shield electrode ink layer by a 1 mil layer 54 of epoxy. On the inner surface of the disk 12 is disposed a 40-mil-thick brass electrode 56, which is the "hot" electrode of the transducer (i.e., the electrode through which electrical energy is supplied to the copolymer transducer to cause the transducer to transmit ultrasonic energy) and is bonded by a 1 mil epoxy layer 58 to the inner surface of the inner copolymer layer 28.

The inner sleeve 14b of the housing is laterally surrounded, on its outer surface, by a 10-mil-thick copper shield 62 which is in electrical contact, at its outer extremity, with the silver ink shield electrode layer 52. At the inner end of sleeve 14b there is provided a 5 mil brass shield electrode 64 secured by 1-mil-thick adhesive 66 to the inner edge of the sleeve and connected electrically to the copper shield 62 by a 5-mil-thick ring 68 of silver ink.

The hot brass electrode 56 is connected to external circuitry by a shielded cable 70 which extends into the rear surface of the cup member 14a through a potted seal 72 and includes a shield braid wire 74 soldered to the brass shield electrode 64 as well as a hot lead 76. The lead 76, extending within the inner housing sleeve 14b, is bonded by silver epoxy to the brass electrode 56.

FIGS. 10A–10D show an illustrative specific example of the receiver transducer 11. The receiver transducer housing may be essentially identical to that of the transmitter transducer described above, including a rigid molded plastic outer cup member 18a and inner housing member 18b with a strain relief feature 18c; the periphery of the receiver transducer disk 16 overlies the outer edge of sleeve 18b and is secured by a potted seal 18d to the rim of the cup member 18a.

In this receiver transducer, the disk 16 is a laminate of four layers 78, 80, 82 and 84 of the P(VDF-TrFE)(75/25) copolymer, each 230 μm (9 mils) thick, bonded to each other by 1 mil layers 86, 88, 90 of epoxy. A 5-mil-thick silver ink shield electrode layer 92 extends over the outer face of the outermost copolymer layer 78 and around the peripheral side edge of the laminate. The inner surface of the innermost copolymer layer 84 is secured around its periphery by a 1 mil epoxy layer 94 to the edge of sleeve 18b; and a 40-mil-thick hot brass electrode 96 is bonded by a 1 mil epoxy layer 98 to the central portion of the inner surface of copolymer layer 84.

A copper shield 108, 10 mils thick, laterally surrounds the sleeve 18b and is in electrical contact with the silver ink shield electrode layer 92. At the inner end of sleeve 18b there is provided a 5 mil brass shield electrode 112 secured by 1-mil-thick adhesive 114 to the inner edge of the sleeve and connected electrically to the copper shield 108 by a 5-mil-thick ring 116 of silver ink.

The hot brass electrode 96 is connected to external circuitry by a shielded cable 118 which extends into the rear surface of the cup member 18a through a potted seal 124 and includes a shield braid wire 126 soldered to the brass shield electrode 112 as well as a hot lead 128. The lead 128, extending within the inner housing sleeve 18b, is bonded by silver epoxy to the brass electrode 96.

Figure 13:
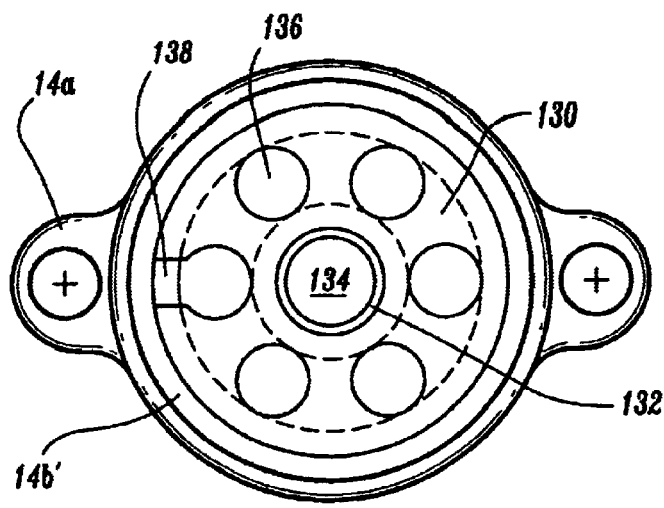
FIG. 13 is a plan view of the housing and support elements incorporated in the transducers of FIG. 11 and FIG. 12, with the copolymer transducer elements omitted.
Figure 11:
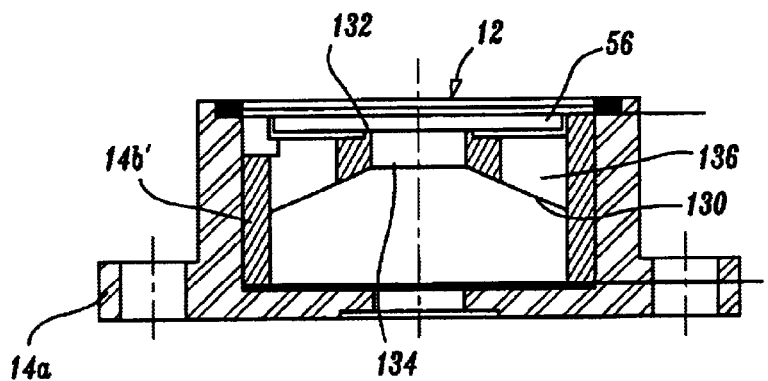
FIG. 11 is a sectional view, similar to FIG. 9B, of a modified and preferred structure of the copolymer transmitter transducer of the invention.
Figure 12:
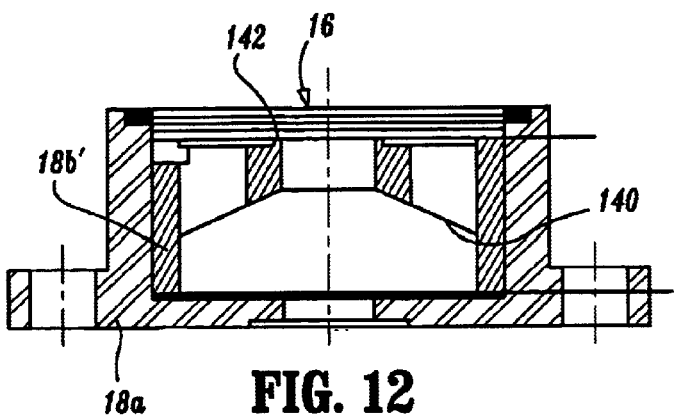
FIG. 12 is a sectional view, similar to FIG. 10B, of a modified and preferred structure of the copolymer receiver transducer of the invention.

As a further particular feature of the invention, shown in FIGS. 11–13, but not in FIGS. 9A–10D discussed above, the inner sleeves of the two transducer housings each include a support structure for engaging the inwardly-facing surface of the associated transducer disk, inwardly of the periphery of the disk, for supporting the disk against pressure exerted on the outwardly-facing surface of the disk. As will be apparent from FIG. 6, when a patient's heel is inserted between the two pad units 150 and the transducers are positionally adjusted as described above with reference to FIG. 3, so that the transducers are ultrasonically coupled to the heel, pressure is exerted by the pads 150 on the transducer disks 12, 16 which they respectively engage. Such pressure could cause deformation of the disks, interfering with proper operation of the apparatus and/or resulting in damage such as disruption of bonding.

Specifically, in the transmitter transducer of FIG. 11, the inner sleeve 14b of the housing shown in FIGS. 9A–9D is replaced by a rigid molded plastic sleeve 14b' including a rigid central spider portion 130, molded integrally with the outer wall of the sleeve, and formed with a thin but rigid outwardly projecting central annulus or ring 132 disposed to engage the inwardly facing surface of the brass electrode 56 when the disk 12 including electrode 56 is in planar, unstressed condition. The ring 132 is concentric with the cylindrical outer wall of the sleeve 14b' and with the disk periphery, but spaced inwardly therefrom, so as to engage the electrode surface in a narrow annular region. Within the ring 132, the spider portion 130 has a central aperture 134, and has a plurality of other apertures 136 regularly disposed around the ring, radially outwardly thereof. A notch 138 may be provided in one of the outer apertures 136 to accommodate the hot lead wire 76.

The receiver transducer of FIG. 12 has an inner housing sleeve 18b' essentially identical to the sleeve 14b' of FIG. 11. Thus, it includes an integrally molded rigid spider portion 140 providing a narrow, outwardly projecting ring 142 disposed in concentric, inwardly spaced relation to the outer wall of sleeve 18b' for engaging the inwardly-facing electrode surface of the receiver transducer disk 16 when the latter is in planar, unstressed condition. In plan view, the spider portions of both sleeves 14b' and 18b', have the appearance illustrated in FIG. 13, which represents sleeve 14b'.

The rings 132 and 142 provide distributed rigid support acting against the inner surfaces of disks 12 and 16, respectively, so as to resist deformation of the disks by pressure exerted by the pad units 150 during operation of the apparatus, yet without impairing the transducer function of the disks. Such support has not been necessary in the case of conventional ceramic piezoelectric transducer elements, but avoids a potential problem of distortion or deformation that might otherwise be encountered in the use of plate-shaped piezoelectric copolymer transducers in ultrasonic bone-testing apparatus.

Stated more generally, it is currently deemed convenient or preferable that the piezoelectric copolymer transducers (transmitter and receiver) utilized in the invention have the following characteristics and properties:

| | |
|---|---|
| center frequency | 630 KHz ± 20% |
| diameter of active element | 0.75" ± 0.1" |
| eccentricity of active element with respect to housing | 0.010" maximum concentric to outer assembly |
| voltage rating | 1000 volts (transmitter) |
| capacitance (including cable) | 95 ± 10 pF (transmitter) 80 ± 10 pF (receiver) |
| shunt resistance | >10 MΩ DC @1000 v. |
| operating temp. | 15–40° C. |
| storage temp. | –40–60° C. |

Figure 9A:
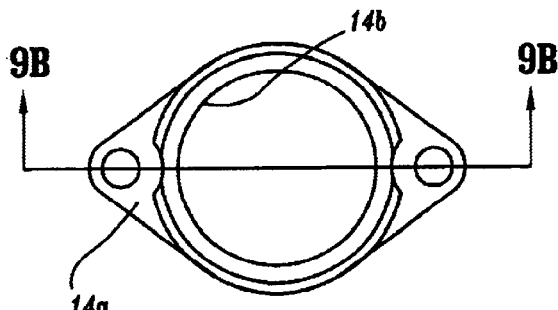
FIG. 9A is an end view of the copolymer transmitter transducer of FIG. 6.
Figure 9C:
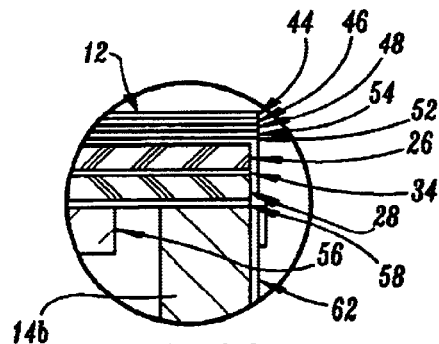
FIG. 9C is an enlarged sectional view of the portion indicated by circle 9C in FIG. 9B.
Figure 9B:
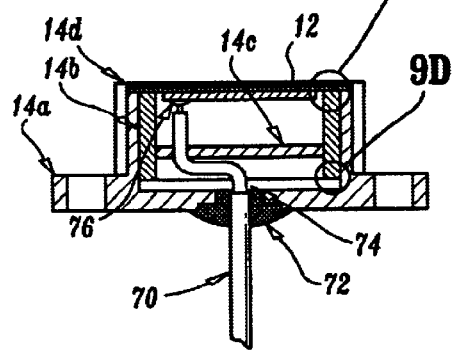
FIG. 9B is a sectional view taken along line 9B—9B of FIG. 9A.
Figure 9D:
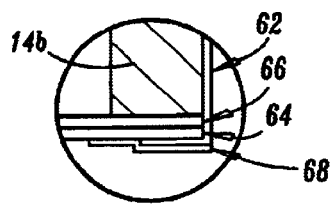
FIG. 9D is a similarly enlarged sectional view of the portion indicated by circle 9D in FIG. 9B.
Figure 10A:
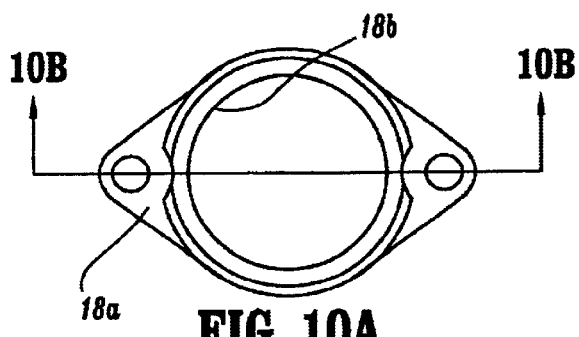
FIG. 10A is an end view of the copolymer receiver transducer of FIG. 6.
Figure 10C:
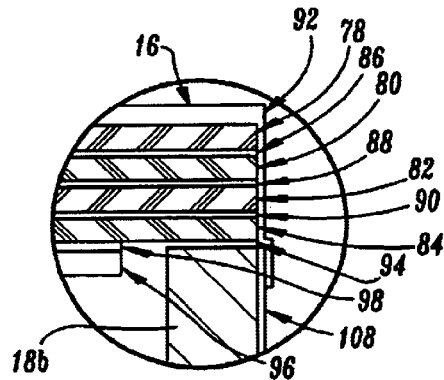
FIG. 10C is an enlarged sectional view of the portion indicated by circle 10C in FIG. 10B.
Figure 10B:
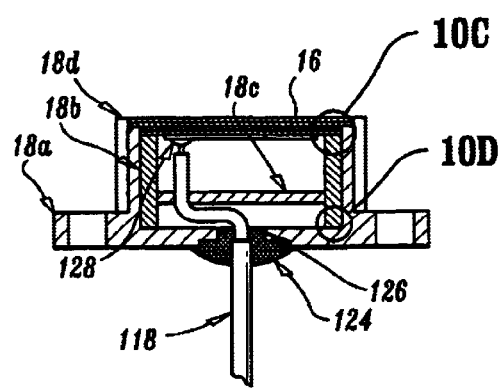
FIG. 10B is a sectional view taken along line 10B—10B of FIG. 10A.
Figure 10D:
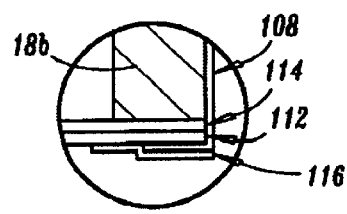
FIG. 10D is a similarly enlarged sectional view of the portion indicated by circle 10D in FIG. 10B.

In addition to the examples of transducers described above with reference to FIGS. 9A–9D and 10A–10D, further illustrative examples of structures suitable for the transmitter disk 12 and receiver disk 16 are as follows:

(a) a structure as shown in FIG. 9B, in which polycarbonate layer 44 is 0.60 mm (about 24 mils) thick, aluminum layer 48 is 0.95 mm (about 38 mils) thick, and copolymer layers 26 and 28 with the intervening epoxy layer 34 are replaced by a single layer of the P(VDF-TrFE)(75/25) copolymer 100 $\mu$m (about 4 mils) thick;

(b) a structure as shown in FIG. 9B, in which polycarbonate layer 44 is 0.60 mm (about 24 mils) thick, aluminum layer 48 is omitted, and copolymer layers 26 and 28 with the intervening epoxy layer 34 are replaced by a single layer of the P(VDF-TrFE)(75/25) copolymer 230 $\mu$m (about 9 mils) thick; and (c) a structure as shown in FIG. 9B, in which polycarbonate layer 44 is 0.55 mm (about 22 mils) thick, aluminum layer 48 is 0.60 mm (about 24 mils) thick, and copolymer layers 26 and 28 with the intervening epoxy layer 34 are replaced by a single layer of the P(VDF-TrFE)(75/25) copolymer 230 $\mu$m (about 9 mils) thick.

Each of these disk structures (a), (b) and (c) also included a 1 mm (about 40 mil) thick brass electrode 56 arranged as shown in FIG. 9B.

When tested, each of structures (a), (b) and (c) was found to be slightly better than the structures of the disks 12 and 16 described above with reference to FIGS. 9A–9D and 10A–10D (two samples of structure (c) were included in the tests). Structure (b) had a wider bandwidth than the others (including the structures of FIGS. 9A–9D and 10A–10D), but has more signal in the 1–3 MHz range, which is not wanted or needed for bone testing operations; it has, however, the advantage of a 3-layer design, which reduces the number of manufacturing steps and bonding layers. Structure (a) peaked at a higher frequency than the others (including the structures of FIGS. 9A–9D and 10A–10D), but has the advantage of using a thinner, hence less expensive and more easily manufactured, copolymer transducer layer. Further, it was found that transducers having the disk 12 or 16 structures (a), (b) and (c) described above, and those of FIGS. 9A–9D and 10A–10D, exhibited no difference in tested performance characteristics when used as transmitters and as receivers.

Figure 8A:
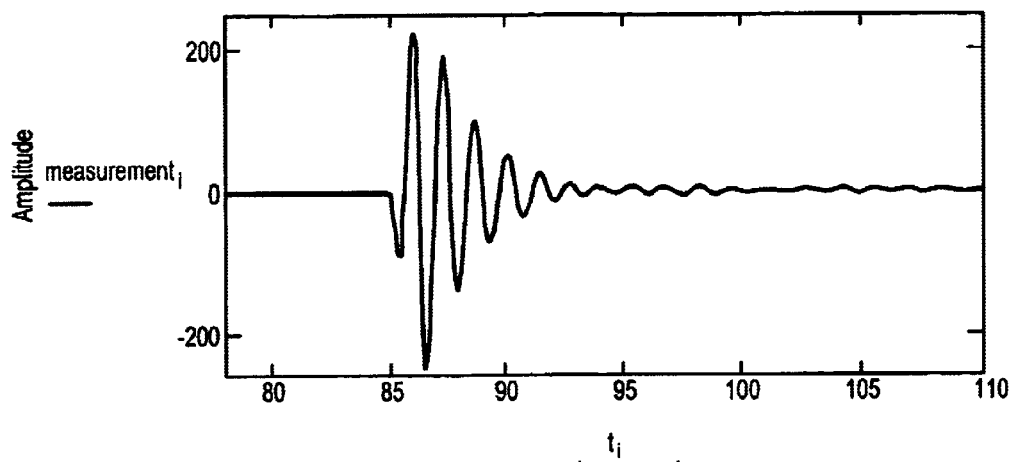
FIGS. 8A, 8B and 8C are graphs showing response curves for the currently preferred embodiment of the receiver/transmitter pair of transducers for the last-mentioned embodiment of the invention.
Figure 8B:
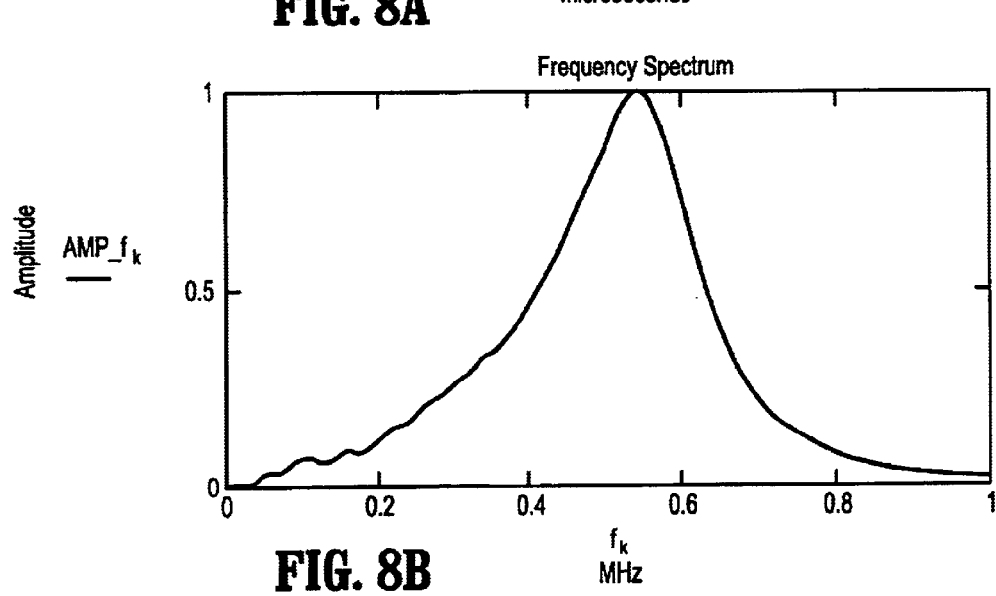
Figure 8C:
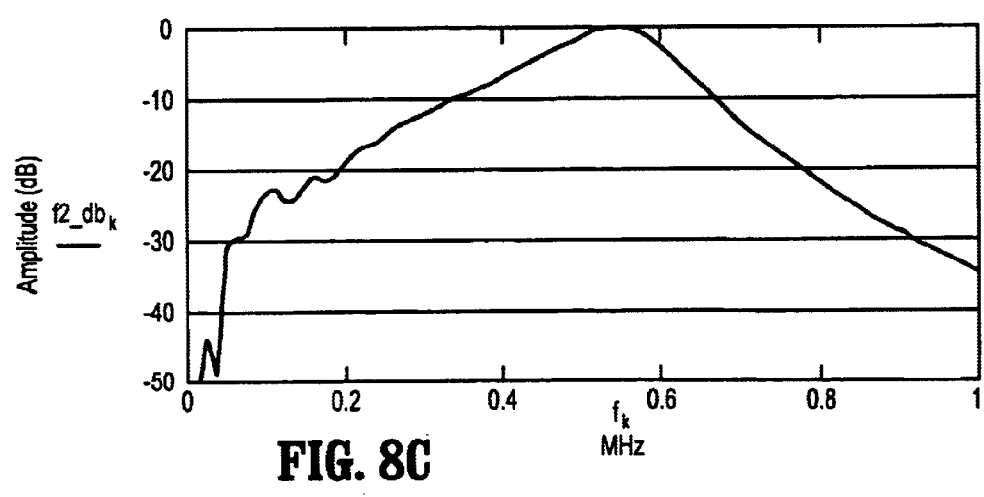

The currently most preferred copolymer transducer for the apparatus of the invention, primarily for reasons of cost, has a backing of 1 mm brass, one layer of 230 μm thick copolymer, 0.025 inch of aluminum and 0.020 inch of polycarbonate. Identical transducers are used for the receiver and the transmitter. Response curves for this transducer pair are shown in FIGS. 8A–8C.

It is currently considered desirable to use a low-pass filter incorporated in the receive electronics to prevent aliasing, and in such case, it is currently believed preferable to use a transducer having disk structure (b) described above in combination with a transducer having disk structure (a), (b) or (c) described above.

The piezoelectric copolymer transducers of the invention function, like the ceramic piezoelectric crystals heretofore used in ultrasonic bone testing apparatus, to transmit ultrasonic energy through a bone to be tested, e.g. the calcaneal bone of a human heel (in the case of the apparatus embodiment shown in FIGS. 1–5), and to receive the transmitted ultrasonic signal and produce, in response thereto, an electrical signal which is detected and used to derive a value representative of the bone characteristic (such as bone mineral density, BMD) to be determined. Typically, in such ultrasonic bone testing apparatus using the copolymer transducers, BMD is determined by measuring the speed of sound (SOS) through the heel and/or the broadband ultrasonic attenuation (BUA), in known manner, as has heretofore been practiced with apparatus employing conventional ceramic piezoelectric crystal transducers.

Alternative Dry System

Figure 14:
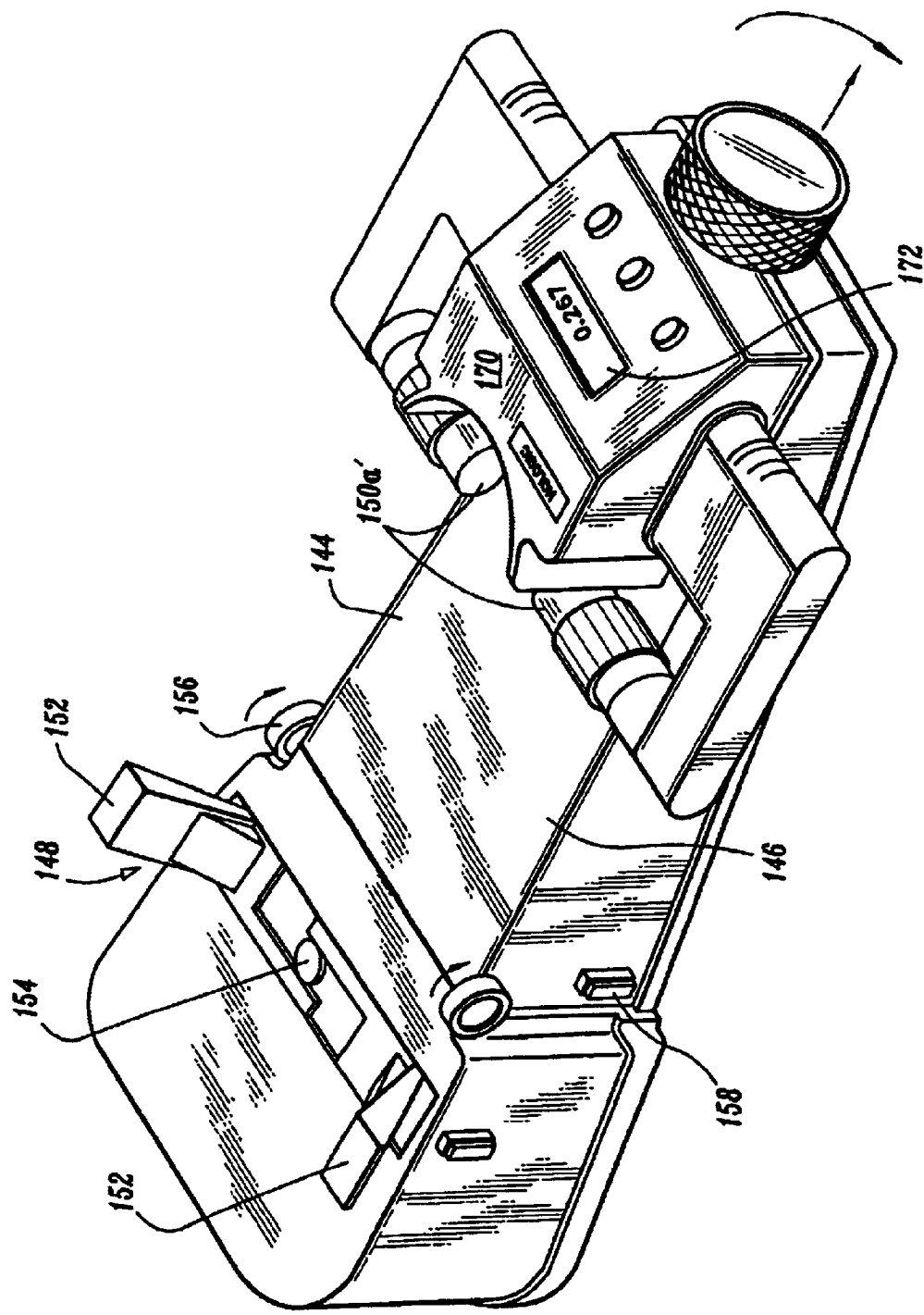
FIG. 14 is a perspective view of another dry system type of ultrasonic bone testing apparatus in which the present invention may be embodied.
Figures 15A, 15B:
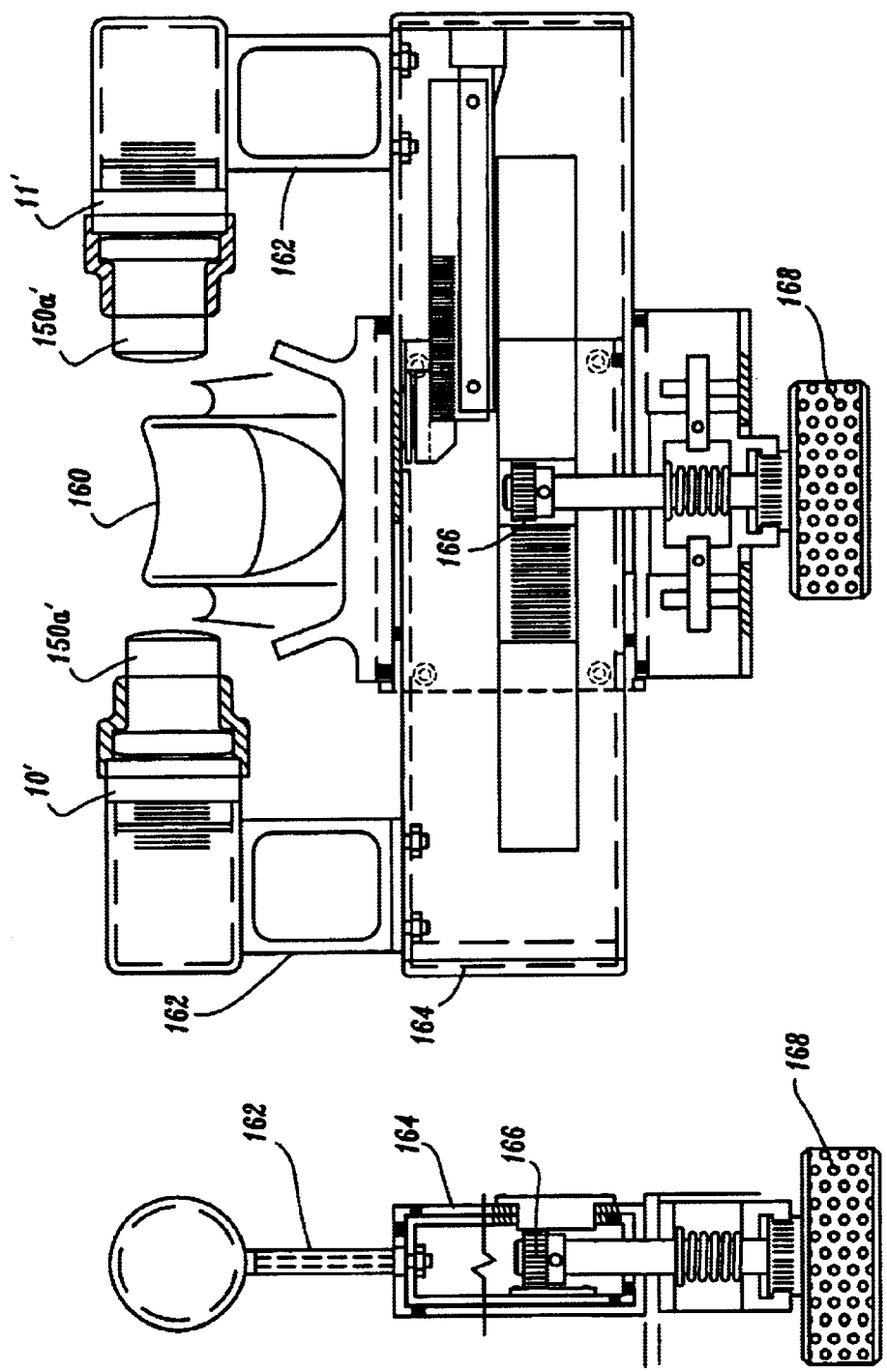
FIG. 15A is a sectional plan view of the apparatus of FIG. 14.
FIG. 15B is a sectional elevational view of the apparatus of FIG. 14.

Another example of dry-type apparatus for testing the calcaneal (heel) bone of living human subjects or patients, in which the present invention may be embodied, is shown in FIGS. 14–15B. In this embodiment, which is designed to be small and highly compact, a base 144 is provided with an inclined surface 146 on which the foot of a human patient is placed. In the forward (upper) portion of the inclined surface there is mounted a foot positioner mechanism 148 comprising a pair of upward projections 152 carried on a mechanism 154 for moving the projections laterally toward and away from each other, into and out of engagement with the forward portion of a foot resting on the surface 146, to locate and stably retain the foot on the surface. The base can be folded about a pivot 156 for storage and transport; to permit such folding, a button 158 releases a latch (not shown) that holds the base open for use.

As shown in FIG. 15A, at the rear (low) end of the surface 146, a transmitter transducer 10' and receiver transducer 11' are mounted, generally in the same relationship to each other as the transducers 101 in FIG. 3, together with pad units 150a' for ultrasonically coupling the transducers to opposite sides of a patient's heel. The apparatus further includes a molded heel rest 160, positioned to locate the heel between the transducers. The transducers are mounted on arms 162 carried on a telescoping structure 164 operated by a gear and toothed track mechanism 166 under control of a manually rotatable wheel 168 so that the arms 162 are laterally movable toward and away from each other.

The transducers 10' and 11' may be piezoelectric copolymer transducers having the same composition and structure as the transducers 10 and 11 described above. In this highly simplified machine, the circuitry and processing unit (not shown) are contained within a housing 170 at the rear of the base, and a numerical data measurement is displayed, for example, by an LED device 172.

Wet System

In another embodiment of the invention, the above-described copolymer transducers may be incorporated in "wet" apparatus wherein the patient's heel is immersed in a liquid bath which ultrasonically couples the heel to the transducers.

Figure 16:
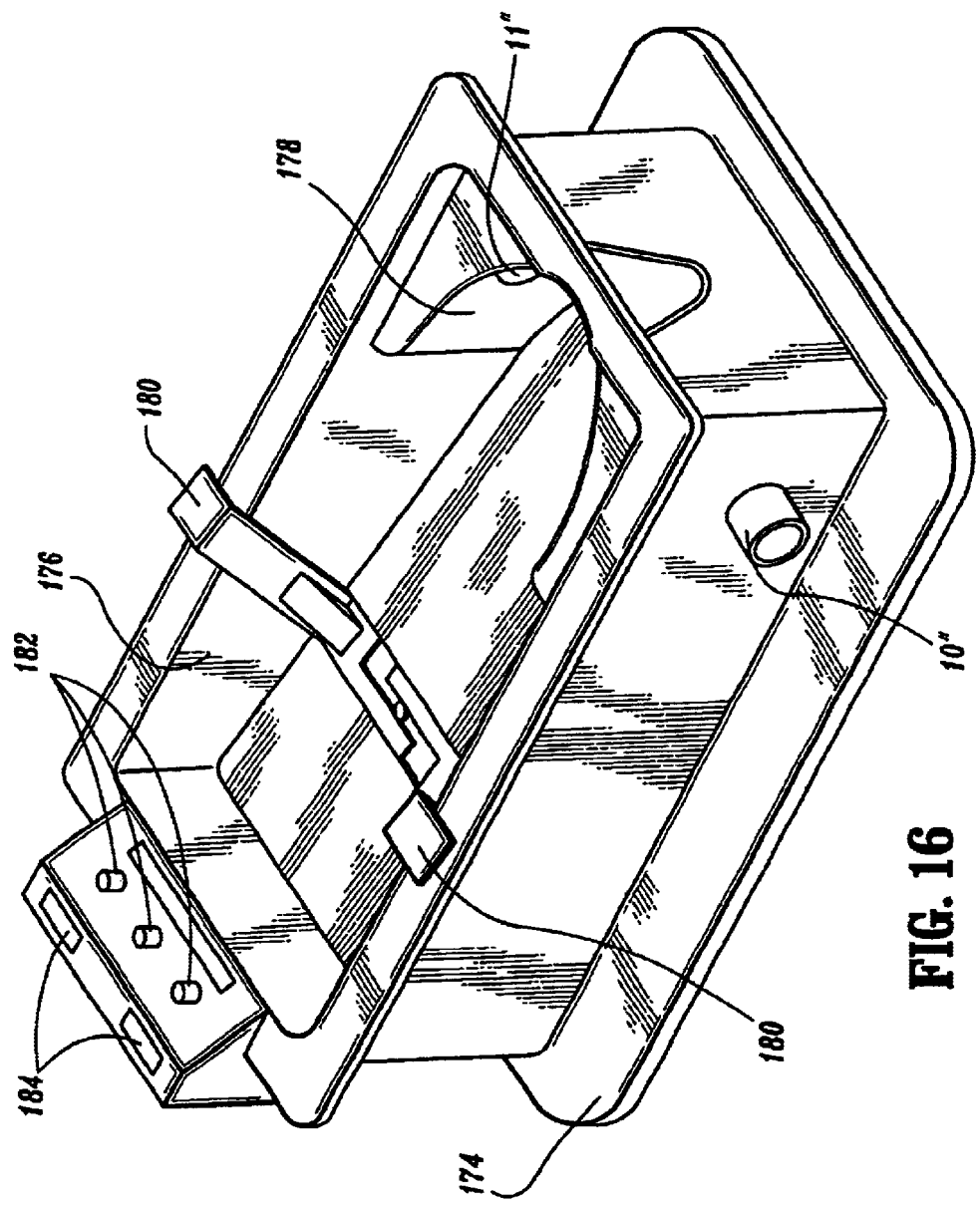
FIG. 16 is a perspective view of a wet system type of ultrasonic bone testing apparatus in which the present invention may be embodied.

An example of such apparatus is illustrated in FIG. 16. A base 174 includes a receptacle 176 for holding a body of liquid, the receptacle being dimensioned to receive a human patient's foot and having a rear inner wall portion 178 shaped to receive the heel. At a forward location within the receptacle is a foot positioner similar to the positioner 148 of FIG. 14 including laterally movable projections 180 for engaging opposite sides of the foot.

A transmitter transducer 10" and a receiver transducer 11" are mounted in the rearward portion of the base, being respectively positioned on opposite sides of the receptacle in the rearward portion in which the patient's heel is placed. These transducers are piezoelectric copolymer transducers again having essentially the same composition and structure as the transducers 10 and 11 described above. They face each other through the body of liquid contained in the receptacle, being ultrasonically coupled to the liquid and aligned to transmit ultrasonic energy through the calcaneal bone of a heel positioned in the receptacle, and to receive the ultrasonic transmitted energy after it has passed through the heel bone. Controls represented by buttons 182, an LED display or other readout device 184, and electrical circuitry and a processing unit (not shown) are housed in the base.

The performance of bone testing with this device, using the piezoelectric copolymer transducers, may be performed in the same manner as has heretofore been used, for example, to measure BMD in wet-type ultrasonic apparatus with ceramic piezoelectric crystal transducers. Very preferably, the liquid employed in the bath has a speed of sound that is substantially invariant with changes of temperature through a usual range of operating temperatures. Examples of such a liquid are a mixture of water and ethyl alcohol or water and isopropyl alcohol at approximately 17% alcohol by volume.

More generally, in each of the dry and wet systems described above, assessment of BMD may be performed using SOS measurements, BUA measurements, or a combination of both. Measurement of SOS with a particular dry system (that of FIGS. 1–5) is described in detail above. Measurement of SOS in wet ultrasonic systems, and of BUA in both wet and dry ultrasonic systems, is well known to persons skilled in the art, and accordingly need not be further described.

By way of explanation of the combined use of SOS and BUA measurements, a system as shown in FIGS. 1–6 incorporating an embodiment of the present invention can measure SOS (in m/s) and BUA (in dB/MHz) of an ultrasound beam passed through the calcaneus and combine these results linearly to obtain a Quantitative Ultrasound Index (QUI) and an estimate of a patient's heel BMD. While ultrasound parameters do not directly measure BMD, BUA and SOS results are correlated (R=0.82–0.85) with heel BMD results obtained by a standard dual energy x-ray absorptiometry (DXA) technique, as are results for the combined QUI parameter. Thus an estimate of heel BMD results is obtained by a simple linear resealing of the QUI parameter into heel BMD units (in g/cm$^2$).

Particular relationships currently in use are as follows:

$$QUI=0.41(BUA+SOS)-571$$

$$BMD_{est}=0.006323 \cdot QUI-0.07632$$

where SOS is the measured value of speed of sound in m/s, BUA is the measured value of broadband ultrasonic attenuation in dB/MHz, and $BMD_{est}$ is the estimated value of BMD in $g/cm^2$.

Although the copolymer transducers included in the foregoing embodiments of the invention have been shown and described as comprising continuous flat layers or laminae of the copolymer material, other arrangements are also embraced within the broad scope of the invention. For instance, the copolymer material of one or both of the (transmitter and receiver) transducers may have a curved surface to achieve focusing, such curving being facilitated by the ease with which the copolymer material is shaped.

Again, instead of being a continuous transducer, the copolymer transmitter transducer and/or the copolymer receiver transducer used in the system of the invention, for example, may comprise an array of multiple discrete copolymer transducer elements. Such a device is shown schematically in FIGS. 17A and 17B. In this embodiment, the receiver transducer 200 includes a laminate of two continuous layers 202, 204 of the copolymer, with a conducting layer 206 formed on the outer surface of the outer copolymer layer 202 and matching layers 208, 210 overlying the conducting layer 206. Bonding layers 212 and 214 are provided, respectively, between the two copolymer layers and between the two matching layers.

On the inner surface of the inner copolymer layer 204 are provided an array of small, discrete, separated patches 216 of conductive material, each e.g. about 3 mm×3 mm in area. These conductive patches may be applied as by a silkscreen-like operation. Inwardly of them is disposed a backing 218 of insulating high density material such as lead oxide/epoxy. Each of the conductive patches is connected by a separate wire 220 to suitable circuitry, for example circuitry of the type hereinafter described.

The circuitry for a copolymer array detector receiver (having the transducer arrangement shown in FIGS. 17A and 17B) is shown schematically in FIGS. 18A–18F.

The detector, as described above, is divided into a number of segments that may be arranged to form a Cartesian array (rectangular matrix) or any other pattern compatible with the system in which the detector is used. These segments are created by depositing mutually isolated elements of metal on a copolymer substrate or by etching away parts of a metal layer deposited continuously on such a substrate. The technology used for this purpose is similar in many respects to the technology developed for the purpose of manufacturing printed wiring assemblies and is well known to those skilled in the art.

Alternatively, a copolymer array transducer may be produced by providing an array of discrete conductive patches (metal elements) on an extended surface of a circuit board (instead of depositing the metal on a surface of the copolymer sheet or substrate), and adhering the copolymer sheet or substrate in overlying relation to the array-bearing circuit board surface with a thin bonding layer such that there is capacitive coupling between the copolymer substrate and the array of conductive patches. This arrangement is advantageous, for piezoelectric sheet transducers generally, from the standpoint of manufacturing convenience and ease of providing electrical connections (through the circuit board) to the individual patches of the array.

Corresponding to the detector array produced by one of the techniques described above is an array of preamplifier input stages consisting of an input transistor, a feedback resistor, a feedback capacitor, a pulldown resistor, and a switch. The input transistor is preferably a junction type field-effect transistor, either P-channel or N-channel, with a very high transconductance, a low pinch-off voltage, and a very low gate current. The feedback resistor is preferably a resistor of high value, for example 10 megohm. The feedback capacitor is preferably a stable capacitor of very low value, for example 5 to 10 picofarad. The pulldown resistor is a resistor suitable for pulling the feedback network to a voltage at which the input transistor is cut off when the switch is open, for example 100 kilohm. The switch is a semiconductor device capable of connecting or disconnecting the output of the output stage described hereafter from the feedback resistor and feedback capacitor in response to a digital control signal.

In addition to the array of preamplifier input stages the system also include one or more preamplifier output stages. Each preamplifier output stage has an input terminal biased to a voltage appropriate for the collector or drain of the input stage input transistor. Also connected to this input terminal is a current source appropriate for providing the drain current of the input stage input transistor. A number of the drains or collectors of the input stage input transistors are connected together and to the input terminal of one of the preamplifier output stages. If only one output stage is provided, all input stage input transistor drains or collectors are connected to the one output stage input terminal. If more than one output stage is provided, some input stage input transistor drains or collectors are connected to each output stage input terminal but not in such a way that two or more output stage input terminals are connected together.

The configuration of the output stage is such as to provide an inverting configuration in combination with any one of the input stages. The output of each output stage is connected to the free terminal of the switches associated with the input stages connected to the input of that output stage. Thus, by activating (closing) one switch, a full preamplifier is created consisting of the input stage corresponding to the activated switch and the corresponding output stage. The output terminal of each output stage is connected to external circuits for further processing in accordance with the desired conventions.

The switches associated with each preamplifier input stage (and, therefore, with each element in the sensor array) may be controlled directly by external data processing equipment or within the preamplifier system by an array of decoders operating on the output of a counter or counters that may (but need not) be internal to the preamplifier.

In the preferred implementation the preamplifier system is fabricated in such a manner as to provide an integrated detector/preamplifier module. Modern multi-layer printed wiring technology is well suited for this purpose. The parts necessary can be made available as subminiature "chip" components. Connections and interconnections can be established using "vias" when necessary. The number of interface connections is easily manageable.

Figure 17A:
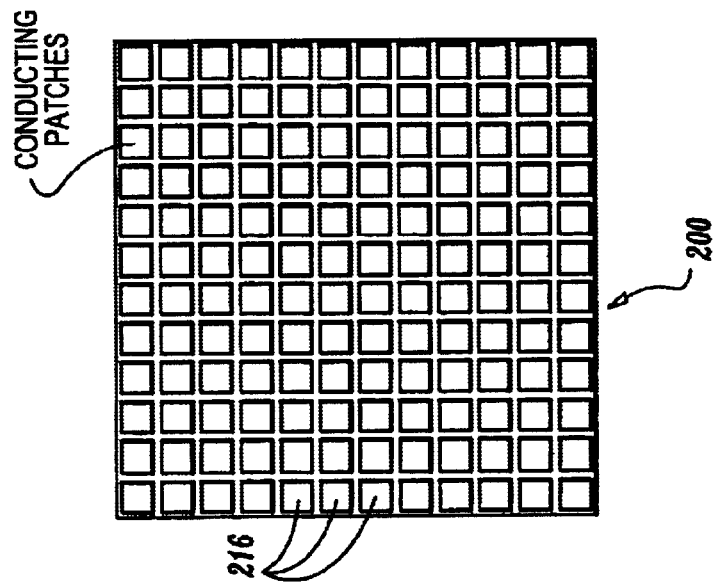
FIGS. 17A and 17B are respectively a plan view and a schematic side sectional view of a copolymer transducer receiver arranged for use as an array of multiple discrete elements.
Figure 17B:
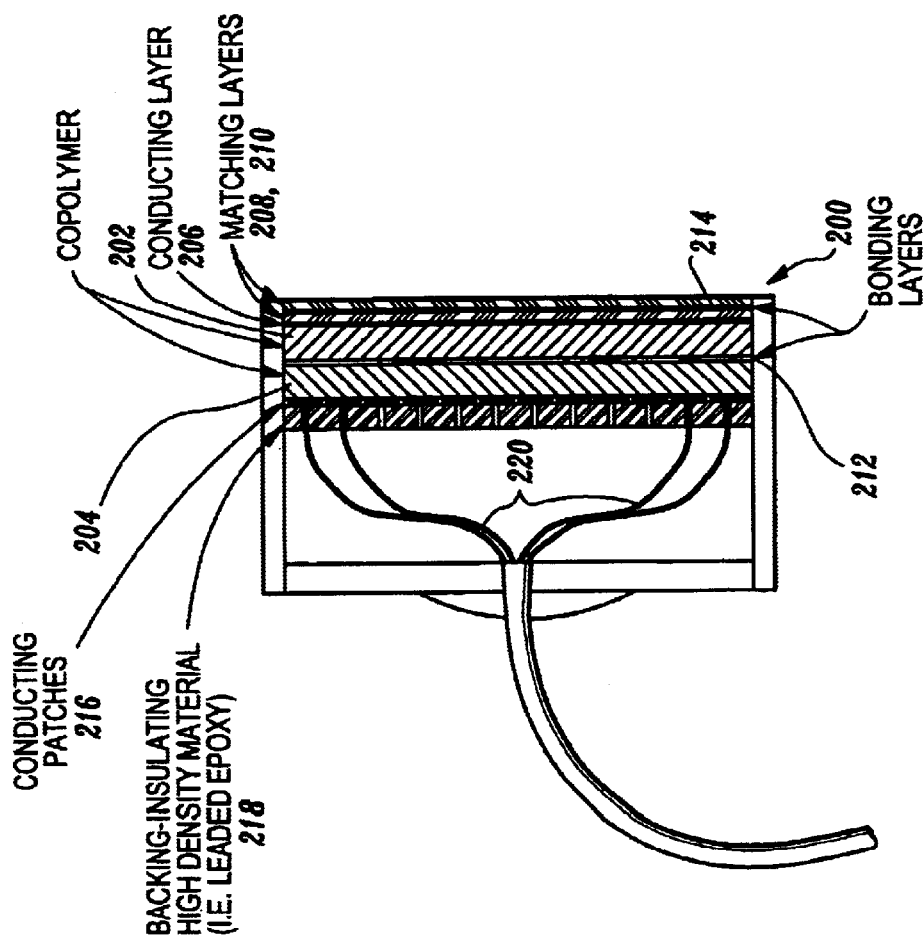

With such an array as illustratively exemplified by the embodiment shown in FIGS. 17A and 17B and described above, it is possible to correct for phase cancellation. The phenomenon of phase cancellation, and its effect on accuracy of BUA measurements, are discussed by Petley et al., Brit. J. Radiol. 68:1212–14 (1995). The nature of the copolymer material, as contrasted with conventional piezoelectric materials, facilitates production of an array transducer.

Copolymer array transducers as just described may also be employed for imaging, i.e., in use of the system of the present invention to produce images. Each discrete patch or element of copolymer may be considered to correspond to a pixel of an image to be produced. Each pixel, in such case, could have a different BUA, SOS or BMD value. Thus, in this broad sense, the invention embraces apparatus in which at least one of the copolymer transducers employed is an array of discrete copolymer transducer elements, such a transducer being herein termed a copolymer array transducer. Illustratively, the receiver transducer of the apparatus would be a copolymer array transducer, used with a transmitter transducer which might be a single unitary copolymer transducer or might be a conventional (non-copolymer) transducer or, advantageously, is itself a copolymer array transducer. Also, the method of the invention embraces methods for producing an image wherein at least one of the transducers employed is a copolymer array transducer as defined above.

Copolymer arrays are discussed by Goldberg et al., *Ultrasonic Imaging* 14:234–48 (1992). Ultrasonic densitometers with transducer arrays including a piezoelectric sheet of polyvinylidene fluoride are discussed in U.S. Pat. No. 5,840,029.

Bladder System

A further example of apparatus for testing the calcaneal (heel) bone of living human subjects or patients is described in U.S. Pat. No. 5,772,596, the entire disclosure of which is incorporated herein by this reference. As there set forth, an osteoporosis apparatus for measuring ultrasonic characteristic (s) of a patient's bone comprises two ultrasonic transducers spacedly positioned in respective heads in the apparatus for ultrasonic transmission from one to the other; circuitry for controlling transmission from the one transducer, measuring the reception at the other and providing an output indicative of the ultrasonic characteristics(s); the apparatus including: two diaphragms positioned in the respective heads; structural spacing means that permits the diaphragms to be brought in contact with the patient's bone so that there is a fluid path from each transducer to its diaphragm and a gap between the diaphragms which is occupied in use by the patient's bone, wherein the diaphragms are connected by a fluid system which is adapted to be pressurized for adjustment of the diaphragms by inflation against the patient's bone. The fluid may, for example, be water.

In apparatus of the described type, a variety of specific different forms and features may be provided. Thus, as further set forth in U.S. Pat. No. 5,772,596, the apparatus may include a sensor for sensing the temperature of the fluid, with the circuitry being adapted to compensate the measurements for the temperature, although preferably the apparatus uses a fluid (such as an alcohol-water mixture) that has a speed of sound substantially independent of temperature. The apparatus may have means for adjustably spacing the transducers in the apparatus so as to provide a standard length of fluid path. Again, the apparatus may include means for fixedly spacing the transducers in the apparatus and may further have means for adjusting the diaphragms relative to each other so as to accommodate differing thicknesses of the patient's bone. The diaphragms may be mounted on annular supports with outer annular sleeves provided around the supports for limiting radial inflation of the diaphragms, with the diaphragms and annular supports being carried on respective tubes having advancement means for adjustment of the apparatus to suit patients having differing bone thicknesses, and the tubes being threaded and adapted for diaphragm advance by screw action.

The tubes may be resilient for extension under fluid pressure for diaphragm advance, having concertina formations for their resilient extension. Each diaphragm and respective concertina formations may be formed as a single moulding of resilient plastics material and may include a peripheral bead engaging in a circumferential groove in the respective head for securing of the diaphragm to the head.

The fluid system may include a fluid interconnection between the fluid paths to each transducer for diaphragm pressure equalization, the apparatus having means for arranging the fluid interconnection so as to avoid ultrasound transmission along the fluid interconnection. Again, the fluid system may be divided into separate portions, one for each transducer. The fluid system may be open, the diaphragms being flexible and the apparatus including hydraulic head biasing means for biasing the diaphragms into contact with the patient's bone; or the fluid system may be closed or closable and provided with means for pressurization, whereby the diaphragms can be urged into contact with the patient. Such pressurization means may be an air pump arranged to pump air into a region of the fluid system higher than the transducers and the diaphragms.

The present invention may be embodied in apparatus of the type described in U.S. Pat. No. 5,772,596, by providing, as at least one of the two ultrasonic transducers in such apparatus, a transducer comprising a piezoelectric polymer. Preferably, in these embodiments, at least one of the transducers is a copolymer array transducer. More preferably both are copolymer array transducers.

It is to be understood that the invention is not limited to the features and embodiments hereinabove specifically set forth, but may be carried out in other ways without departure from its spirit.

What is claimed is:

1. Ultrasonic bone testing apparatus comprising a pair of ultrasonic transducers each of which comprises a piezoelectric copolymer transducer; mounting structure supporting the transducers in facing spaced relation to each other, so as to be respectively positionable on opposite sides of and both coupled ultrasonically to an animal portion containing a bone, for respectively transmitting ultrasonic energy through and receiving ultrasonic energy transmitted through said animal portion including the bone; and electrical circuitry connected to the transducers to energize one transducer to transmit ultrasonic energy and to detect an electrical signal generated by the other transducer in response to received ultrasonic energy, wherein the mounting structure includes a support for positioning the animal portion between the transducers, and a device for coupling the transducers ultrasonically to the animal portion; and wherein each of the transducers comprises a copolymer disk having a periphery and two opposed major surfaces, one of which is disposed to face the bone-containing animal portion, and further includes rigid support structure engaging the other major surface of the disk inwardly of the periphery thereof for supporting the disk against pressure exerted on the first-mentioned major surface of the disk.

2. Ultrasonic bone testing apparatus comprising a pair of ultrasonic transducers each of which comprises a piezoelectric copolymer transducer; mounting structure supporting the transducers in facing spaced relation to each other, so as to be respectively positionable on opposite sides of and both coupled ultrasonically to an animal portion containing a bone, for respectively transmitting ultrasonic energy through and receiving ultrasonic energy transmitted through said animal portion including the bone; and electrical circuitry connected to the transducers to energize one transducer to transmit ultrasonic energy and to detect an electrical signal generated by the other transducer in response to received ultrasonic energy, wherein the mounting structure includes a support for positioning the animal portion between the transducers, and a device for coupling the transducers ultrasonically to the animal portion; wherein said coupling device comprises a pair of pads, respectively disposed in contact with said transducers, and respectively engageable with opposed surface regions of an animal portion positioned in said support as aforesaid; and wherein each of said transducers comprises a copolymer disk having a periphery and opposed major surfaces, one of which is in contact with one of said pads, and further includes rigid support structure engaging the other major surface of the disk inwardly of the periphery thereof for supporting the disk against pressure exerted on the disk through the last-mentioned pad.

3. A method of determining a characteristic of a bone in a bone-containing portion of an animal comprising disposing a pair of ultrasonic transducers each of which comprises a piezoelectric copolymer transducer respectively on opposite sides of, and ultrasonically coupling both transducers to, a bone-containing animal portion; electrically energizing one transducer to transmit ultrasonic energy through the animal portion including the bone, such that the transmitted ultrasonic energy is received and converted to an electrical signal by the other transducer; detecting the electrical signal; and using the detected signal to derive a value representative of the bone characteristic to be determined; wherein each of the transducers is a disk of piezoelectric copolymer; and wherein each transducer disk has a periphery and opposed major surfaces, one of which is oriented to face the animal portion, and further including supporting the other major surface of each disk by disposing, in contact therewith, rigid support structure spaced inwardly from the disk periphery.

* * * * *